United States Patent
Tzvieli et al.

(10) Patent No.: US 10,376,163 B1
(45) Date of Patent: Aug. 13, 2019

(54) BLOOD PRESSURE FROM INWARD-FACING HEAD-MOUNTED CAMERAS

(71) Applicant: Facense Ltd., Kiryat Tivon (IL)

(72) Inventors: Arie Tzvieli, Berkeley, CA (US); Ari M Frank, Haifa (IL); Ori Tzvieli, Berkeley, CA (US); Gil Thieberger, Kiryat Tivon (IL)

(73) Assignee: Facense Ltd., Kiryat Tivon (IL)

( * ) Notice: Subject to any disclaimer, the term of this patent is extended or adjusted under 35 U.S.C. 154(b) by 0 days.

(21) Appl. No.: 16/375,841

(22) Filed: Apr. 4, 2019

Related U.S. Application Data

(63) Continuation-in-part of application No. 16/156,493, filed on Oct. 10, 2018, which is a continuation-in-part
(Continued)

(51) Int. Cl.
*A61B 5/024* (2006.01)
*A61B 5/00* (2006.01)
(Continued)

(52) U.S. Cl.
CPC ........ *A61B 5/02416* (2013.01); *A61B 5/0077* (2013.01); *A61B 5/0295* (2013.01);
(Continued)

(58) Field of Classification Search
CPC ..... A61B 5/0077; A61B 5/0075; A61B 5/165; A61B 5/6803; A61B 5/7282; A61B 5/746;
(Continued)

(56) References Cited

U.S. PATENT DOCUMENTS

| 5,757,002 A | 5/1998 | Yamasaki et al. |
| 8,175,670 B2 | 5/2012 | Baker, Jr. et al. |
(Continued)

OTHER PUBLICATIONS

Samria, R., Jain, R., Jha, A., Saini, S., & Chowdhury, S. R. (Apr. 2014). Noninvasive cuffless estimation of blood pressure using Photoplethysmography without electrocardiograph measurement. In 2014 IEEE Region 10 Symposium (pp. 254-257). IEEE.
(Continued)

*Primary Examiner* — David P Porta
*Assistant Examiner* — Fani Boosalis
(74) *Attorney, Agent, or Firm* — Active Knowledge Ltd.

(57) ABSTRACT

A system for detecting blood pressure based on imaging photoplethysmography (iPPG) includes a first inward-facing head-mounted camera to capture images of a first region of interest located on the face below the eyes and above the lips ($IM_{ROI1}$) of a user, and a second inward-facing head-mounted camera to capture images of a second region of interest comprising a portion of a temple and/or forehead ($IM_{ROI2}$) of the user. The system further includes a computer to calculate a blood pressure value for the user based on first and second photoplethysmographic signals recognizable in $IM_{ROI1}$ and $IM_{ROI2}$.

20 Claims, 10 Drawing Sheets

Related U.S. Application Data of application No. 15/635,178, filed on Jun. 27, 2017, now Pat. No. 10,136,856, and a continuation-in-part of application No. 15/231,276, filed on Aug. 8, 2016, and a continuation-in-part of application No. 15/832,855, filed on Dec. 6, 2017, now Pat. No. 10,130,308, which is a continuation-in-part of application No. 15/182,592, filed on Jun. 14, 2016, now Pat. No. 10,165,949, and a continuation-in-part of application No. 15/231,276, filed on Aug. 8, 2016, and a continuation-in-part of application No. 15/284,528, filed on Oct. 3, 2016, now Pat. No. 10,113,913, and a continuation-in-part of application No. 15/635,178, filed on Jun. 27, 2017, now Pat. No. 10,136,856, and a continuation-in-part of application No. 15/722,434, filed on Oct. 2, 2017, and a continuation-in-part of application No. 15/182,566, filed on Jun. 14, 2016, now Pat. No. 9,867,546, said application No. 16/156,493 is a continuation-in-part of application No. 15/833,115, filed on Dec. 6, 2017, now Pat. No. 10,130,261, which is a continuation-in-part of application No. 15/182,592, filed on Jun. 14, 2016, now Pat. No. 10,165,949, and a continuation-in-part of application No. 15/231,276, filed on Aug. 8, 2016, and a continuation-in-part of application No. 15/284,528, filed on Oct. 3, 2016, now Pat. No. 10,113,913, and a continuation-in-part of application No. 15/635,178, filed on Jun. 27, 2017, now Pat. No. 10,136,856, and a continuation-in-part of application No. 15/722,434, filed on Oct. 2, 2017.

(60) Provisional application No. 62/354,833, filed on Jun. 27, 2016, provisional application No. 62/372,063, filed on Aug. 8, 2016, provisional application No. 62/652,348, filed on Apr. 4, 2018, provisional application No. 62/667,453, filed on May 5, 2018, provisional application No. 62/202,808, filed on Aug. 8, 2015, provisional application No. 62/236,868, filed on Oct. 3, 2015, provisional application No. 62/456,105, filed on Feb. 7, 2017, provisional application No. 62/480,496, filed on Apr. 2, 2017, provisional application No. 62/566,572, filed on Oct. 2, 2017, provisional application No. 62/175,319, filed on Jun. 14, 2015.

(51) Int. Cl.
*A61B 5/0295* (2006.01)
*G02B 27/01* (2006.01)
*A61B 5/026* (2006.01)

(52) U.S. Cl.
CPC .......... *A61B 5/6821* (2013.01); *G02B 27/017* (2013.01); *A61B 5/0002* (2013.01); *A61B 5/0064* (2013.01); *A61B 5/0261* (2013.01); *A61B 5/6826* (2013.01); *A61B 5/6831* (2013.01); *G02B 2027/0178* (2013.01)

(58) Field of Classification Search
CPC ........ A61B 2503/12; A61B 2565/0233; A61B 2562/0271; A61B 2562/046; A61B 5/0816; A61B 5/0823; A61B 5/0878; A61B 5/091; A61B 5/486; A61B 5/7275; A61B 7/003; A61B 5/01; A61B 5/021; A61B 5/02055; A61B 5/11; A61B 5/14551; A61B 5/02416; A61B 5/026; A61B 5/6898; A61B 2503/20; A61B 3/18; A61B 5/0002; A61B 5/0046; A61B 5/02007; A61B 5/0261; A61B 5/0295; A61B 5/0531; A61B 5/6819; A61B 5/0404; A61B 5/150022; A61B 5/150343; G02B 27/017; G02B 2027/0178

See application file for complete search history.

(56) References Cited

U.S. PATENT DOCUMENTS

| | | | |
|---|---|---|---|
| 8,251,903 | B2 | 8/2012 | LeBoeuf et al. |
| 8,617,081 | B2 | 12/2013 | Mestha et al. |
| 8,768,438 | B2 | 7/2014 | Mestha et al. |
| 8,855,384 | B2 | 10/2014 | Kyal et al. |
| 8,977,347 | B2 | 3/2015 | Mestha et al. |
| 9,020,185 | B2 | 4/2015 | Mestha et al. |
| 9,044,180 | B2 | 6/2015 | LeBoeuf et al. |
| 9,220,856 | B2 | 12/2015 | Martin et al. |
| 9,414,769 | B2 | 8/2016 | Karst et al. |
| 9,610,035 | B2 | 4/2017 | Aarts et al. |
| 9,805,475 | B2 | 10/2017 | Rubinstein et al. |
| 9,808,204 | B2 | 11/2017 | LeBoeuf et al. |
| 9,848,780 | B1 | 12/2017 | DeBusschere et al. |
| 9,940,710 | B2 | 4/2018 | Watanabe |
| 2007/0276632 | A1 | 11/2007 | Banet et al. |
| 2010/0168589 | A1 | 7/2010 | Banet et al. |
| 2010/0241011 | A1 | 9/2010 | McCombie et al. |
| 2012/0029320 | A1 | 2/2012 | Watson et al. |
| 2013/0215244 | A1 | 8/2013 | Mestha et al. |
| 2014/0213917 | A1 | 7/2014 | Hobeika et al. |
| 2015/0005646 | A1 | 1/2015 | Balakrishnan et al. |
| 2015/0112606 | A1 | 4/2015 | He et al. |
| 2015/0297126 | A1 | 10/2015 | Atsumori et al. |
| 2016/0022157 | A1 | 1/2016 | Melker et al. |
| 2016/0081622 | A1* | 3/2016 | Abreu ............... A61B 5/0002 600/549 |
| 2016/0098592 | A1 | 4/2016 | Lee et al. |
| 2016/0120411 | A1 | 5/2016 | Hadley et al. |
| 2016/0302677 | A1 | 10/2016 | He |
| 2017/0007167 | A1 | 1/2017 | Kostic et al. |
| 2017/0011210 | A1 | 1/2017 | Cheong et al. |
| 2017/0112376 | A1 | 4/2017 | Gill et al. |
| 2017/0202505 | A1 | 7/2017 | Kirenko et al. |
| 2017/0367590 | A1 | 12/2017 | Sebe et al. |
| 2018/0031372 | A1 | 2/2018 | Gill |
| 2018/0143458 | A1* | 5/2018 | Blum ..................... G02C 11/10 |
| 2018/0146870 | A1 | 5/2018 | Shemesh et al. |
| 2018/0177416 | A1 | 6/2018 | Church et al. |
| 2018/0192950 | A1 | 7/2018 | LeBoeuf et al. |
| 2018/0199870 | A1 | 7/2018 | Lee et al. |
| 2018/0206733 | A1 | 7/2018 | Kasan et al. |
| 2018/0206735 | A1* | 7/2018 | Holz ................... A61B 5/0205 |
| 2018/0214079 | A1 | 8/2018 | Banet et al. |
| 2018/0314879 | A1 | 11/2018 | Khwaja et al. |

OTHER PUBLICATIONS

Zaunseder, S., Trumpp, A., Wedekind, D., & Malberg, H. (2018). Cardiovascular assessment by imaging photoplethysmography—a review. Biomedical Engineering/Biomedizinische Technik, 63(5), 617-634.

Shao, D., Tsow, F., Liu, C., Yang, Y., & Tao, N. (2017). Simultaneous monitoring of ballistocardiogram and photoplethysmogram using a camera. IEEE Transactions on Biomedical Engineering, 64(5), 1003-1010.

Rouast, P. V., Adam, M. T., Chiong, R., Cornforth, D., & Lux, E. (2018). Remote heart rate measurement using low-cost RGB face video: a technical literature review. Frontiers of Computer Science, 12(5), 858-872.

McDuff, D. J., Estepp, J. R., Piasecki, A. M., & Blackford, E. B. (Aug. 2015). A survey of remote optical photoplethysmographic imaging methods. In 2015 37th annual international conference of the IEEE engineering in medicine and biology society (EMBC) (pp. 6398-6404). IEEE.

(56) References Cited

OTHER PUBLICATIONS

Moco, A. V., Stuijk, S., & De Haan, G. (2016). Ballistocardiographic artifacts in PPG imaging. Jeff Transactions on Biomedical Engineering, 63(9), 1804-1811.

Mcduff, D., Hurter, C., & Gonzalez-Franco, M. (Nov. 2017). Pulse and vital sign measurement in mixed reality using a HoloLens. In Proceedings of the 23rd ACM Symposium on Virtual Reality Software and Technology (p. 34). ACM.

Kong, L., Zhao, Y., Dong, L., Jian, Y., Jin, X., Li, B., . . . & Wu, H. (2013). Non-contact detection of oxygen saturation based on visible light imaging device using ambient light. Optics express, 21(15), 17464-17471.

Al-Naji, A., Gibson, K., Lee, S. H., & Chahl, J. (2017). Monitoring of cardiorespiratory signal: Principles of remote measurements and review of methods. IEEE Access, 5, 15776-15790.

Fung, P., Dumont, G., Ries, C., Mott, C., & Ansermino, M. (Sep. 2004). Continuous noninvasive blood pressure measurement by pulse transit time. In the 26th annual international conference of the IEEE engineering in medicine and biology society (vol. 1, pp. 738-741). IEEE.

Shirbani, F., Blackmore, C., Kazzi, C., Tan, I., Butlin, M., & Avolio, A. P. (Jul. 2018). Sensitivity of Video-Based Pulse Arrival Time to Dynamic Blood Pressure Changes. In 2018 40th Annual International Conference of the IEEE Engineering in Medicine and Biology Society (EMBC) (pp. 3639-3641). IEEE.

Buxi, D., Redoute, J. M., & Yuce, M. R. (2015). A survey on signals and systems in ambulatory blood pressure monitoring using pulse transit time. Physiological measurement, 36(3), R1.

Avolio, A. P., Butlin, M., & Walsh, A. (2009). Arterial blood pressure measurement and pulse wave analysis—their role in enhancing cardiovascular assessment. Physiological measurement, 31(1), R1.

Song, S. H., Cho, J. S., Oh, H. S., Lee, J. S., & Kim, I. Y. (Sep. 2009). Estimation of blood pressure using photoplethysmography on the wrist. In 2009 36th Annual Computers in Cardiology Conference (CinC) (pp. 741-744). IEEE.

Sun, Y., & Thakor, N. (2016). Photoplethysmography revisited: from contact to noncontact, from point to imaging. IEEE Transactions on Biomedical Engineering, 63(3), 463-477.

Corral, F., Paez, G., & Strojnik, M. (2014). A photoplethysmographic imaging system with supplementary capabilities. Optica Applicata, 44(2).

Allen, J. (2007). Photoplethysmography and its application in clinical physiological measurement. Physiological measurement, 28(3), R1.

Callego, E. C., & de Haan, G. (Mar. 2015). Automatic ROI for remote photoplethysmography using PPG and color features. In 10th International Conference on Computer Vision Theory and Applications VISAPP-2015.

Po, L. M., Feng, L., Li, Y., Xu, X., Cheung, T. C. H., & Cheung, K. W. (2018). Block-based adaptive ROI for remote photoplethysmography. Multimedia Tools and Applications, 77(6), 6503-6529.

Huang, P. W., Lin, C. H., Chung, M. L., Lin, T. M., & Wu, B. F. (Nov. 2017). Image based contactless blood pressure assessment using Pulse Transit Time. In 2017 International Automatic Control Conference (CACS) (pp. 1-6). IEEE.

Ramirez, G. A., Fuentes, O., Crites Jr, S. L., Jimenez, M., & Ordonez, J. (2014). Color analysis of facial skin: Detection of emotional state. In Proceedings of the IEEE Conference on Computer Vision and Pattern Recognition Workshops (pp. 468-473).

Solà, J., Proença, M., Braun, F., Pierrel, N., Degiorgis, Y., Verjus, C., . . . & Schoettker, P. (2016). Continuous non-invasive monitoring of blood pressure in the operating room: a cuffless optical technology at the fingertip. Current Directions in Biomedical Engineering, 2(1), 267-271.

McDuff, D., Gontarek, S., & Picard, R. W. (2014). Improvements in remote cardiopulmonary measurement using a five band digital camera. IEEE Transactions on Biomedical Engineering, 61(10), 2593-2601.

Ballinger, B., Hsieh, J., Singh, A., Sohoni, N., Wang, J., Tison, G. H., . . . & Pletcher, M. J. (Apr. 2018). DeepHeart: semi-supervised sequence learning for cardiovascular risk prediction. In Thirty-Second AAAI Conference on Artificial Intelligence.

Feng, L., Po, L. M., Xu, X., Li, Y., Cheung, C. H., Cheung, K. W., & Yuan, F. (Apr. 2015). Dynamic ROI based on K-means for remote photoplethysmography. In 2015 IEEE International Conference on Acoustics, Speech and Signal Processing (ICASSP) (pp. 1310-1314). IEEE.

Escobar Restrepo, B., Torres Villa, R., & Kyriacou, P. (2018). Evaluation of the Linear Relationship Between Pulse Arrival Time and Blood Pressure in ICU Patients: Potential and Limitations. Frontiers in physiology, 9, 1848.

Jain, M., Deb, S., & Subramanyam, A. V. (Sep. 2016). Face video based touchless blood pressure and heart rate estimation. In 2016 IEEE 18th International Workshop on Multimedia Signal Processing (MMSP) (pp. 1-5). IEEE.

Flament, F., Francois, G., Qiu, H., Ye, C., Hanaya, T., Batisse, D., . . . & Bazin, R. (2015). Facial skin pores: a multiethnic study. Clinical, cosmetic and investigational dermatology, 8, 85.

Holz, C., & Wang, E. J. (2017). Glabella: Continuously sensing blood pressure behavior using an unobtrusive wearable device. Proceedings of the ACM on Interactive, Mobile, Wearable and Ubiquitous Technologies, 1(3), 58.

Ding, X. R., Zhao, N., Yang, G. Z., Pettigrew, R. I., Lo, B., Miao, F., . . . & Zhang, Y. T. (2016). Continuous blood pressure measurement from invasive to unobtrusive: celebration of 200th birth anniversary of Carl Ludwig. IEEE journal of biomedical and health informatics, 20(6), 1455-1465.

Alghoul, K., Alharthi, S., Al Osman, H., & El Saddik, A. (2017). Heart rate variability extraction from videos signals: ICA vs. EVM comparison. IEEE Access, 5, 4711-4719.

Zhang, G., Shan, C., Kirenko, I., Long, X., & Aarts, R. (2017). Hybrid optical unobtrusive blood pressure measurements. Sensors, 17(7), 1541.

Moço, A., Stuijk, S., van Gastel, M., & de Haan, G. (2018). Impairing Factors in Remote-PPG Pulse Transit Time Measurements on the Face. In Proceedings of the IEEE Conference on Computer Vision and Pattern Recognition Workshops (pp. 1358-1366).

Kamshilin, A. A., Miridonov, S., Teplov, V., Saarenheimo, R., & Nippolainen, E. (2011). Photoplethysmographic imaging of high spatial resolution. Biomedical optics express, 2(4), 996-1006.

Ishikawa, T., Hyodo, Y., Miyashita, K., Yoshifuji, K., Komoriya, Y., & Imai, Y. (Feb. 2017). Wearable Motion Tolerant PPG Sensor for Instant Heart Rate in Daily Activity. In Biosignals (pp. 126-133).

Wu, B. F., Huang, P. W., Lin, C. H., Chung, M. L., Tsou, T. Y., & Wu, Y. L. (2018). Motion resistant image-photoplethysmography based on spectral peak tracking algorithm. IEEE Access, 6, 21621-21634.

Liu, J., Yan, B. P. Y., Dai, W. X., Ding, X. R., Zhang, Y. T., & Zhao, N. (2016). Multi-wavelength photoplethysmography method for skin arterial pulse extraction. Biomedical optics express, 7(10), 4313-4326.

Vuksanović, V., Sheppard, L. W., & Stefanovska, A. (2008). Nonlinear relationship between level of blood flow and skin temperature for different dynamics of temperature change. Biophysical journal, 94(10), L78-L80.

Poh, M. Z., McDuff, D. J., & Picard, R. W. (2010). Non-contact, automated cardiac pulse measurements using video imaging and blind source separation. Optics express, 18(10), 10762-10774.

Proença, J., Muehlsteff, J., Aubert, X., & Carvalho, P. (Aug. 2010). Is pulse transit time a good indicator of blood pressure changes during short physical exercise in a young population?. In 2010 Annual International Conference of the IEEE Engineering in Medicine and Biology (pp. 598-601).

Trumpp, A., Rasche, S., Wedekind, D., Rudolf, M., Malberg, H., Matschke, K., & Zaunseder, S. (2017). Relation between pulse pressure and the pulsation strength in camera-based photoplethysmograms. Current Directions in Biomedical Engineering, 3(2), 489-492.

Birrenkott, D. A., Pimentel, M. A., Watkinson, P. J., & Clifton, D. A. (Aug. 2016). Robust estimation of respiratory rate via ECG-and

(56) References Cited

OTHER PUBLICATIONS

PPG-derived respiratory quality indices. In 2016 38th Annual International Conference of the IEEE Engineering in Medicine and Biology Society.(EMBC) (pp. 676-679). IEEE.

Sharma, M., Barbosa, K., Ho, V., Griggs, D., Ghirmai, T., Krishnan, S., . . . & Cao, H. (2017). Cuff-less and continuous blood pressure monitoring: A methodological review. Technologies, 5(2), 21.

Kamshilin, A. A., Teplov, V., Nippolainen, E., Miridonov, S., & Giniatullin, R. (2013). Variability of microcirculation detected by blood pulsation imaging. PloS one, 8(2), e57117.

* cited by examiner

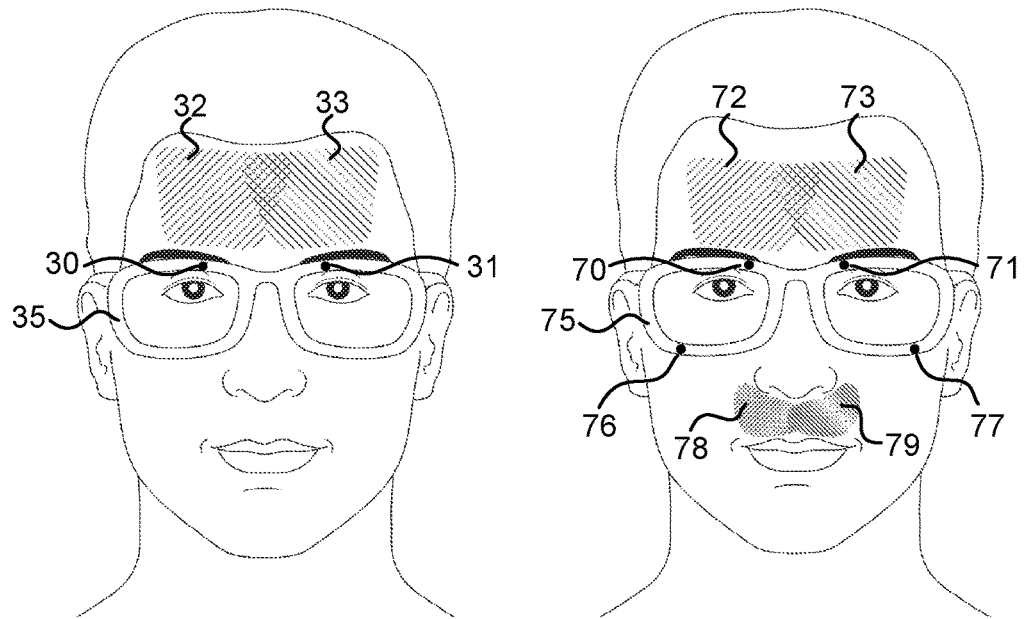
FIG. 6  FIG. 7
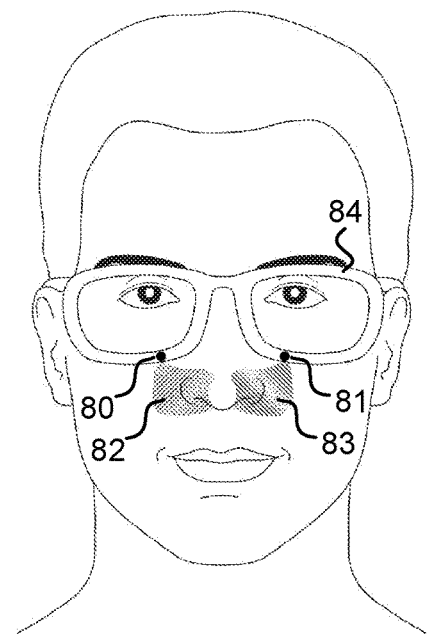 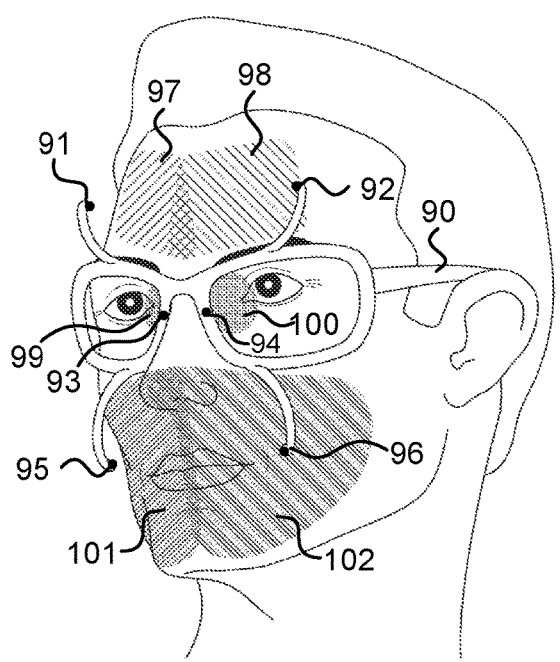
FIG. 8  FIG. 9

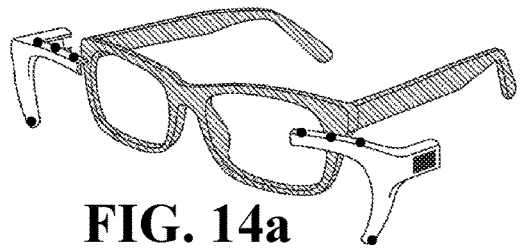
FIG. 14a
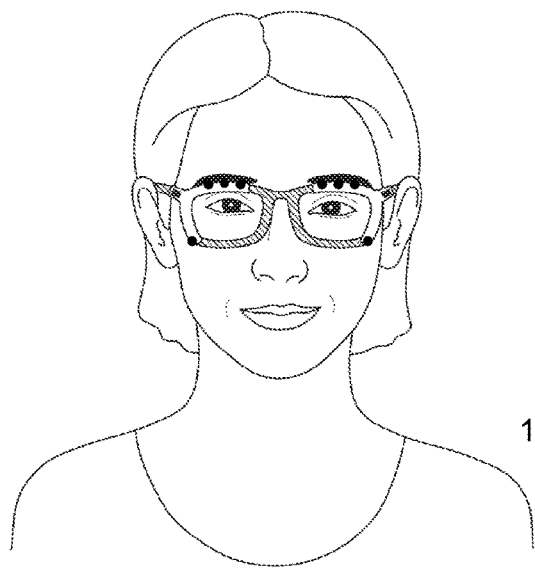
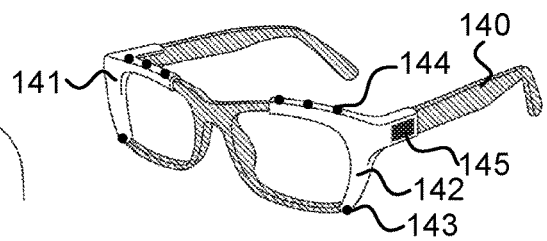
FIG. 14c    FIG. 14b
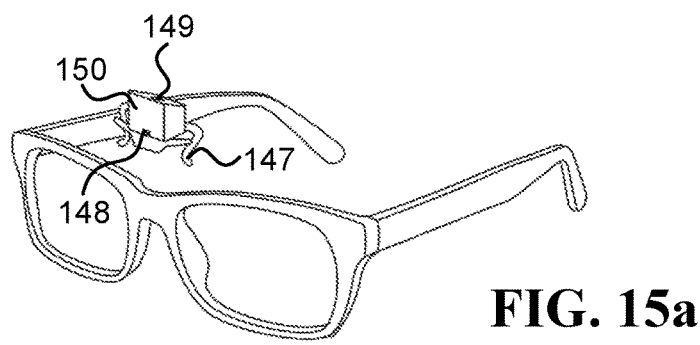
FIG. 15a
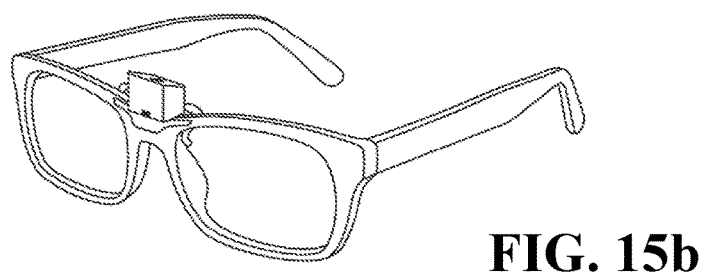
FIG. 15b

BLOOD PRESSURE FROM INWARD-FACING HEAD-MOUNTED CAMERAS

CROSS-REFERENCE TO RELATED APPLICATIONS

This Application claims priority to U.S. Provisional Patent Application No. 62/652,348, filed Apr. 4, 2018 that is herein incorporated by reference in its entirety, and to U.S. Provisional Patent Application No. 62/667,453, filed May 5, 2018 that is herein incorporated by reference in its entirety.

This Application is a Continuation-In-Part of U.S. application Ser. No. 16/156,493, filed Oct. 10, 2018. U.S. Ser. No. 16/156,493, filed Oct. 10, 2018 is a Continuation-In-Part of U.S. application Ser. No. 15/635,178, filed Jun. 27, 2017, now U.S. Pat. No. 10,136,856, which claims priority to U.S. Provisional Patent Application No. 62/354,833, filed Jun. 27, 2016, and U.S. Provisional Patent Application No. 62/372,063, filed Aug. 8, 2016.

U.S. Ser. No. 16/156,493, filed Oct. 10, 2018 is also a Continuation-In-Part of U.S. application Ser. No. 15/231,276, filed Aug. 8, 2016, which claims priority to U.S. Provisional Patent Application No. 62/202,808, filed Aug. 8, 2015, and U.S. Provisional Patent Application No. 62/236,868, filed Oct. 3, 2015.

U.S. Ser. No. 16/156,493, filed Oct. 10, 2018 is also a Continuation-In-Part of U.S. application Ser. No. 15/832,855, filed Dec. 6, 2017, now U.S. Pat. No. 10,130,308, which claims priority to U.S. Provisional Patent Application No. 62/456,105, filed Feb. 7, 2017, and U.S. Provisional Patent Application No. 62/480,496, filed Apr. 2, 2017, and U.S. Provisional Patent Application No. 62/566,572, filed Oct. 2, 2017. U.S. Ser. No. 15/832,855 is a Continuation-In-Part of U.S. application Ser. No. 15/182,592, filed Jun. 14, 2016, now U.S. Pat. No. 10,165,949, a Continuation-In-Part of U.S. application Ser. No. 15/231,276, filed Aug. 8, 2016, a Continuation-In-Part of U.S. application Ser. No. 15/284,528, filed Oct. 3, 2016, now U.S. Pat. No. 10,113,913, a Continuation-In-Part of U.S. application Ser. No. 15/635,178, filed Jun. 27, 2017, now U.S. Pat. No. 10,136,856, and a Continuation-In-Part of U.S. application Ser. No. 15/722,434, filed Oct. 2, 2017.

U.S. Ser. No. 15/832,855 is a Continuation-In-Part of U.S. application Ser. No. 15/182,566, filed Jun. 14, 2016, now U.S. Pat. No. 9,867,546, which claims priority to U.S. Provisional Patent Application No. 62/175,319, filed Jun. 14, 2015, and U.S. Provisional Patent Application No. 62/202,808, filed Aug. 8, 2015.

U.S. Ser. No. 15/182,592, filed Jun. 14, 2016, now U.S. Pat. No. 10,165,949, which claims priority to U.S. Provisional Patent Application No. 62/175,319, filed Jun. 14, 2015, and U.S. Provisional Patent Application No. 62/202,808, filed Aug. 8, 2015.

U.S. Ser. No. 15/284,528, filed Oct. 3, 2016, now U.S. Pat. No. 10,113,913, claims priority to U.S. Provisional Patent Application No. 62/236,868, filed Oct. 3, 2015, and U.S. Provisional Patent Application No. 62/354,833, filed Jun. 27, 2016, and U.S. Provisional Patent Application No. 62/372,063, filed Aug. 8, 2016.

U.S. Ser. No. 16/156,493, filed Oct. 10, 2018 is also a Continuation-In-Part of U.S. application Ser. No. 15/833,115, filed Dec. 6, 2017, now U.S. Pat. No. 10,130,261. U.S. Ser. No. 15/833,115 is a Continuation-In-Part of U.S. application Ser. No. 15/182,592, filed Jun. 14, 2016, now U.S. Pat. No. 10,165,949, a Continuation-In-Part of U.S. application Ser. No. 15/231,276, filed Aug. 8, 2016, a Continuation-In-Part of U.S. application Ser. No. 15/284,528, filed Oct. 3, 2016, now U.S. Pat. No. 10,113,913, a Continuation-In-Part of U.S. application Ser. No. 15/635,178, filed Jun. 27, 2017, now U.S. Pat. No. 10,136,856, and a Continuation-In-Part of U.S. application Ser. No. 15/722,434, filed Oct. 2, 2017.

BACKGROUND

Elevated blood pressure is a significant cause of death and disability in the world. Attaining accurate blood pressure measurements is vital in the prevention and treatment of various blood-pressure-related diseases. However, continuous monitoring with existing blood pressure monitors (e.g., cuff-based devices) can be difficult, uncomfortable, and impractical to perform in real-world settings (e.g., at work, while commuting, etc.). Thus, there is a need to a way to continuously monitor blood pressure in a comfortable way.

SUMMARY

Some aspects of this disclosure include various head-mounted systems (e.g., smartglasses) that measure physiological signals, such as heart rate and/or blood pressure, by analyzing images captured using non-contact head-mounted cameras in a technique often referred to as imaging photoplethysmography (iPPG) or remoted photoplethysmography (rPPG). Blood flow due to a cardiac pulse cause detectible phenomena in captured images of the skin. These changes are generally attributed to blood volume effects (light modulations due to the varying amount of blood in the measured volume) and ballistocardiographic effects (e.g., movements of arteries and skin due to pulsating blood). The image changes due to the pulse can be detected using various techniques, and can enable algorithms to pinpoint when a pulse wave reaches an imaged region of the body. This time is typically referred to as the Pulse Arrival Time (PAT). The speed at which a pulse reaches a region is correlated with the blood pressure; the faster the pulse wave, the higher the blood pressure. The speed at which the pulse travels in the body is also referred to as the Pulse Transit Time (PTT).

Some embodiments described herein involve inward-facing and/or outward facing cameras that are used to capture images of the body which undergo detectable changes due to peripheral blood flow. Analysis of these images can be used to calculate PATs at multiple locations, which can be used to detect various physiological signals, such as heart rate, heart rate variability, and/or blood pressure.

In one embodiment, a system configured to calculate blood pressure includes at least a first inward-facing head-mounted camera ($HCAM_1$) configured to capture images of a first region of interest ($ROI_1$) located on the face below the eyes and above the lips ($IM_{ROI1}$) of a user, and a second inward-facing head-mounted camera ($HCAM_2$) configured to capture images of a second region of interest ($ROI_2$) comprising a portion of a temple and/or forehead ($IM_{ROI2}$) of the user. Optionally, the center of $ROI_1$ is located more than 6 cm away from the center of $ROI_2$; whereby changes in $IM_{ROI1}$ that are due to a cardiac pulse wave occur at least 10 ms before, or at least 10 ms after, changes in $IM_{ROI2}$ occur, which are due to the same cardiac pulse wave. The system also includes a computer configured to calculate a blood pressure value for the user based on first and second imaging photoplethysmographic signals ($iPPG_1$, $iPPG_2$) recognizable in $IM_{ROI1}$ and $IM_{ROI2}$, respectively. Optionally, $iPPG_1$ and $iPPG_2$ are indicative of pulse arrival times at $ROI_1$ and $ROI_2$, respectively. Optionally, the computer is further configured to extract $iPPG_1$ and $iPPG_2$ from $IM_{ROI1}$ and $IM_{ROI2}$, respectively, and to calculate the blood pressure value based on a magnitude of a difference in the pulse arrival times at $ROI_1$ and $ROI_2$. Optionally, the computer is further configured to utilize calibration measurements of the user's blood pressure, taken by a different device, to calculate parameters that are utilized by the computer to calculate the blood pressure value based on $iPPG_1$ and $iPPG_2$; whereby the calibration measurements are indicative of the differences between the pulse arrival times at $ROI_1$ and $ROI_2$ that correspond to different blood pressure values of the user. Optionally, the computer is configured to generate feature values based on data comprising $IM_{ROI1}$ and $IM_{ROI2}$, and to utilize a model to calculate the blood pressure value based on the feature values, where the model was generated based on training data comprising: previously taken $IM_{ROI1}$ and $IM_{ROI2}$, and blood pressure values measured at times corresponding to the previously taken $IM_{ROI1}$ and $IM_{ROI2}$.

BRIEF DESCRIPTION OF THE DRAWINGS

The embodiments are herein described by way of example only, with reference to the following drawings:

FIG. 6, FIG. 7, FIG. 8 and FIG. 9 illustrate head-mounted systems (HMSs) configured to measure various ROIs relevant to some of the embodiments describes herein;

FIG. 14a, FIG. 14b, and FIG. 14c illustrate embodiments of two right and left clip-on devices that are configured to attached/detached from an eyeglasses frame;

FIG. 15a and FIG. 15b illustrate an embodiment of a clip-on device that includes inward-facing head-mounted cameras pointed at the lower part of the face and the forehead;

DETAILED DESCRIPTION

Figure 1A:
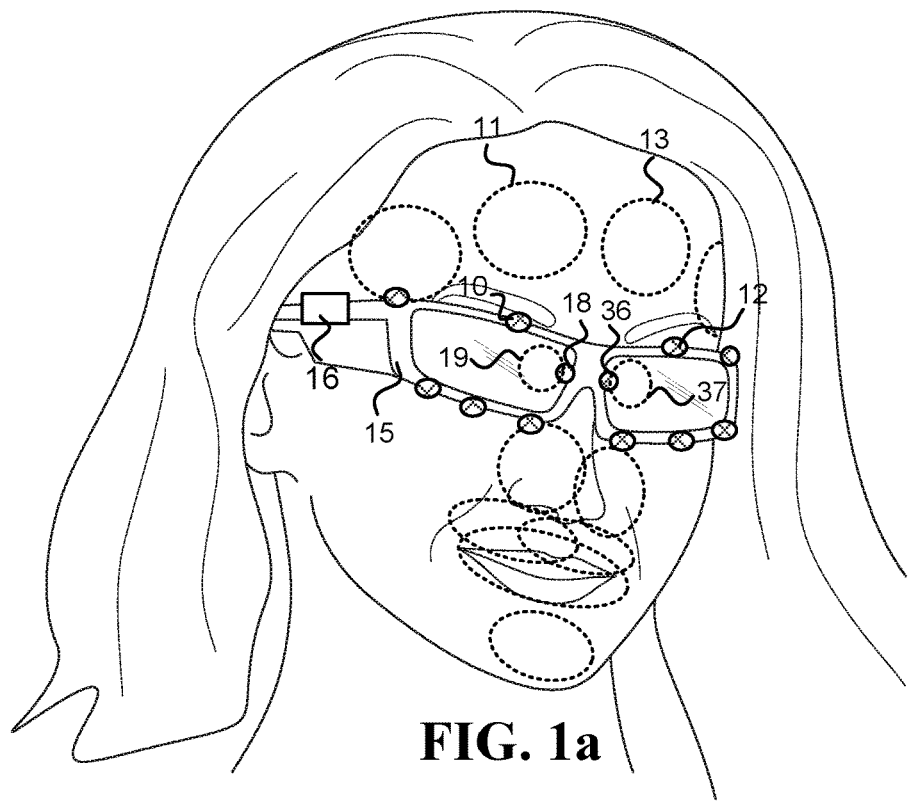
FIG. 1a and FIG. 1b illustrate various inward-facing head-mounted cameras coupled to an eyeglasses frame.

"Visible-light camera" refers to a non-contact device designed to detect at least some of the visible spectrum, such as a video camera with optical lenses and CMOS or CCD sensor. A "thermal camera" refers herein to a non-contact device that measures electromagnetic radiation having wavelengths longer than 2500 nanometer (nm) and does not touch its region of interest (ROI). A thermal camera may include one sensing element (pixel), or multiple sensing elements that are also referred to herein as "sensing pixels", "pixels", and/or focal-plane array (FPA). A thermal camera may be based on an uncooled thermal sensor, such as a thermopile sensor, a microbolometer sensor (where microbolometer refers to any type of a bolometer sensor and its equivalents), a pyroelectric sensor, or a ferroelectric sensor.

A reference to a "camera" herein may relate to various types of devices. In one example, a camera is a visible-light camera. In another example, a camera may capture light in the ultra-violet range. And in another example, a camera may capture near infrared radiation (e.g., wavelengths between 750 and 2000 nm).

In some embodiments, a device, such as a camera, may be positioned such that it occludes an ROI on the user's face, while in other embodiments, the device may be positioned such that it does not occlude the ROI. Sentences in the form of "the system/camera does not occlude the ROI" indicate that the ROI can be observed by a third person located in front of the user and looking at the ROI, such as illustrated by all the ROIs in FIG. 7 and FIG. 11. Sentences in the form of "the system/camera occludes the ROI" indicate that some of the ROIs cannot be observed directly by that third person, such as ROIs 19 and 37 that are occluded by the lenses in FIG. 1a, and ROIs 97 and 102 that are occluded by cameras 91 and 96, respectively, in FIG. 9.

Although some of the disclosed embodiments can use occluding cameras successfully, in certain scenarios, such as when using an HMS on a daily basis and/or in a normal day-to-day setting, using cameras that do not occlude their ROIs on the face may provide one or more advantages to the user, to the HMS, and/or to the cameras, which may relate to one or more of the following: esthetics, better ventilation of the face, reduced weight, simplicity to wear, ability to operate without active illumination, and reduced likelihood to being tarnished.

The term "inward-facing head-mounted camera" refers to a camera configured to be worn on a user's head and to remain pointed at its ROI, which is on the user's face, also when the user's head makes angular and lateral movements (such as movements with an angular velocity above 0.1 rad/sec, above 0.5 rad/sec, and/or above 1 rad/sec). A head-mounted camera (which may be inward-facing and/or outward-facing) may be physically coupled to a frame worn on the user's head, may be attached to eyeglass using a clip-on mechanism (configured to be attached to and detached from the eyeglasses), or may be mounted to the user's head using any other known device that keeps the camera in a fixed position relative to the user's head also when the head moves. Sentences in the form of "camera physically coupled to the frame" mean that the camera moves with the frame, such as when the camera is fixed to (or integrated into) the frame, or when the camera is fixed to (or integrated into) an element that is physically coupled to the frame.

Sentences in the form of "a frame configured to be worn on a user's head" or "a frame worn on a user's head" refer to a mechanical structure that loads more than 50% of its weight on the user's head. For example, an eyeglasses frame may include two temples connected to two rims connected by a bridge; the frame in Oculus Rift™ includes the foam placed on the user's face and the straps; and the frames in Google Glass™ and Spectacles by Snap Inc. are similar to eyeglasses frames. Additionally or alternatively, the frame may connect to, be affixed within, and/or be integrated with, a helmet (e.g., sports, motorcycle, bicycle, and/or combat helmets) and/or a brainwave-measuring headset.

When a camera is inward-facing and head-mounted, challenges faced by systems known in the art that are used to acquire images, which include non-head-mounted cameras, may be simplified and even eliminated with some of the embodiments described herein. Some of these challenges may involve dealing with complications caused by movements of the user, image registration, ROI alignment, tracking based on markers, and/or motion compensation.

In various embodiments, cameras are located close to a user's face, such as at most 2 cm, 5 cm, 10 cm, 15 cm, or 20 cm from the face (herein "cm" denotes to centimeters). The distance from the face/head in sentences such as "a camera located less than 10 cm from the face/head" refers to the shortest possible distance between the camera and the face/head. The head-mounted cameras used in various embodiments may be lightweight, such that each camera weighs below 10 g, 5 g, 1 g, and/or 0.5 g (herein "g" denotes to grams).

Figure 1B:
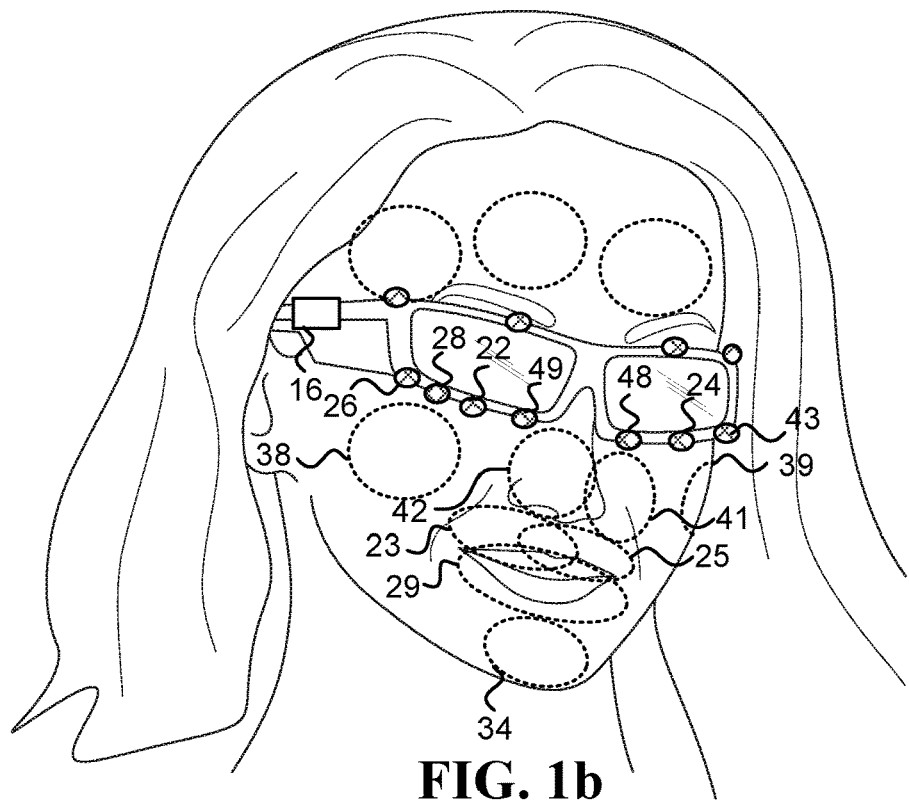

The following figures show various examples of HMSs equipped with head-mounted cameras. FIG. 1a illustrates various inward-facing head-mounted cameras coupled to an eyeglasses frame 15. Cameras 10 and 12 measure regions 11 and 13 on the forehead, respectively. Cameras 18 and 36 measure regions on the periorbital areas 19 and 37, respectively. The HMS further includes an optional computer 16, which may include a processor, memory, a battery and/or a communication module. FIG. 1b illustrates a similar HMS in which inward-facing head-mounted cameras 48 and 49 measure regions 41 and 41, respectively. Cameras 22 and 24 measure regions 23 and 25, respectively. Camera 28 measures region 29. And cameras 26 and 43 measure regions 38 and 39, respectively.

Figure 2:
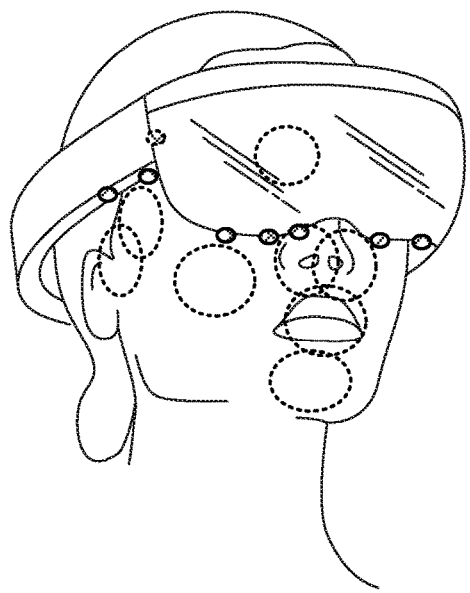
FIG. 2 illustrates inward-facing head-mounted cameras coupled to an augmented reality device.
Figure 3:
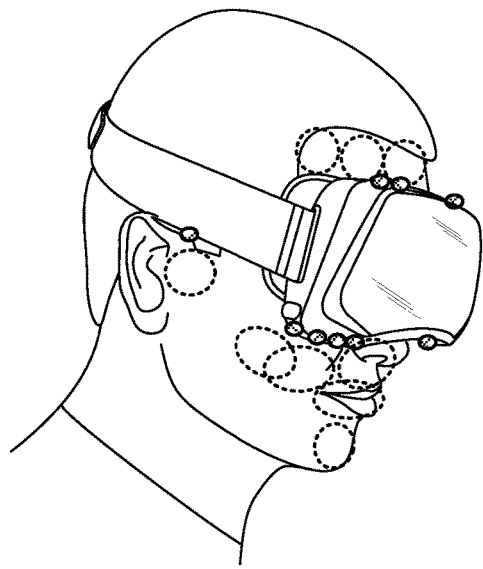
FIG. 3 illustrates head-mounted cameras coupled to a virtual reality device.
Figure 4:
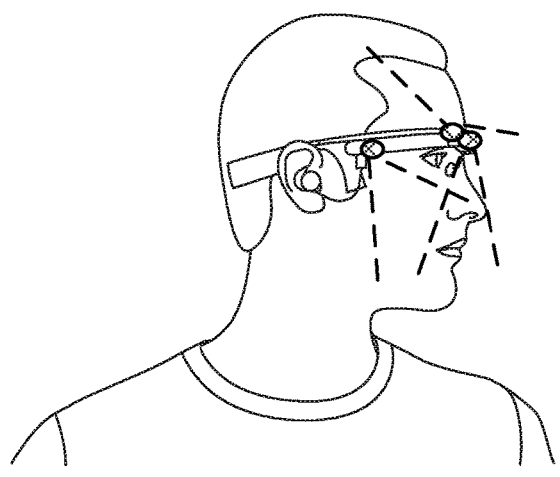
FIG. 4 illustrates a side view of head-mounted cameras coupled to an augmented reality device.
Figure 5:
FIG. 5 illustrates a side view of head-mounted cameras coupled to a sunglasses frame.

FIG. 2 illustrates inward-facing head-mounted cameras coupled to an augmented reality device such as Microsoft HoloLens™. FIG. 3 illustrates head-mounted cameras coupled to a virtual reality device such as Facebook's Oculus Rift™. FIG. 4 is a side view illustration of head-mounted cameras coupled to an augmented reality device such as Google Glass™. FIG. 5 is another side view illustration of head-mounted cameras coupled to a sunglasses frame.

FIG. 6 to FIG. 9 illustrate HMSs configured to measure various ROIs relevant to some of the embodiments describes herein. FIG. 6 illustrates a frame 35 that mounts inward-facing head-mounted cameras 30 and 31 that measure regions 32 and 33 on the forehead, respectively. FIG. 7 illustrates a frame 75 that mounts inward-facing head-mounted cameras 70 and 71 that measure regions 72 and 73 on the forehead, respectively, and inward-facing head-mounted cameras 76 and 77 that measure regions 78 and 79 on the upper lip, respectively. FIG. 8 illustrates a frame 84 that mounts inward-facing head-mounted cameras 80 and 81 that measure regions 82 and 83 on the sides of the nose, respectively. And FIG. 9 illustrates a frame 90 that includes (i) inward-facing head-mounted cameras 91 and 92 that are mounted to protruding arms and measure regions 97 and 98 on the forehead, respectively, (ii) inward-facing head-mounted cameras 95 and 96, which are also mounted to protruding arms, which measure regions 101 and 102 on the lower part of the face, respectively, and (iii) head-mounted cameras 93 and 94 that measure regions on the periorbital areas 99 and 100, respectively.

Figure 10:
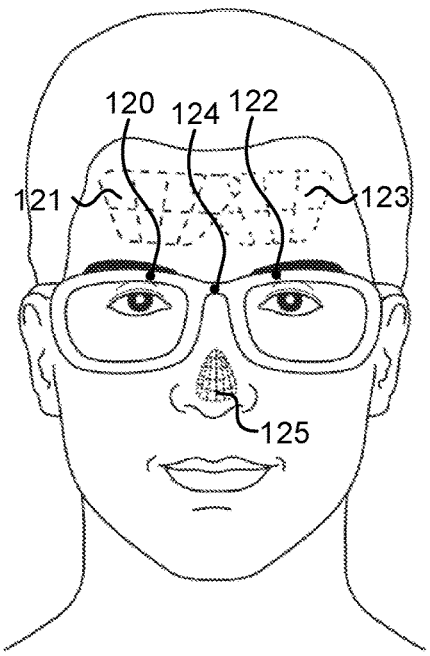
FIG. 10, FIG. 11, FIG. 12 and FIG. 13 illustrate various embodiments of systems that include inward-facing head-mounted cameras having multi-pixel sensors (FPA sensors)
Figure 11:
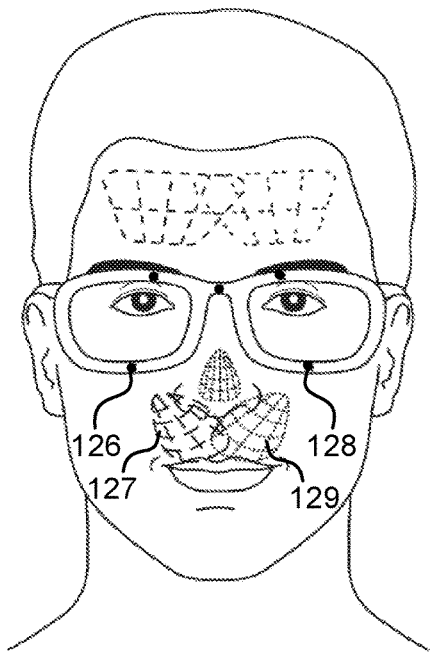
Figure 12:
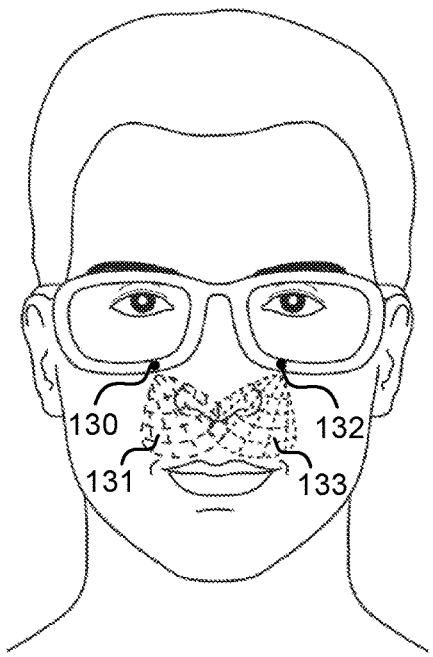
Figure 13:
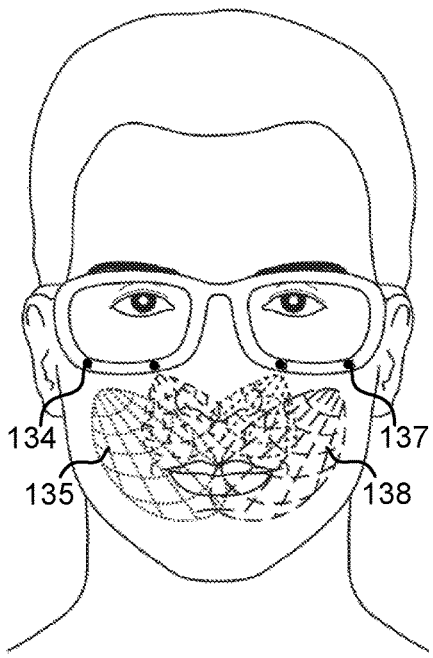

FIG. 10 to FIG. 13 illustrate various inward-facing head-mounted cameras having multi-pixel sensors (FPA sensors), configured to measure various ROIs relevant to some of the embodiments describes herein. FIG. 10 illustrates head-mounted cameras 120 and 122 that measure regions 121 and 123 on the forehead, respectively, and mounts head-mounted camera 124 that measure region 125 on the nose. FIG. 11 illustrates head-mounted cameras 126 and 128 that measure regions 127 and 129 on the upper lip, respectively, in addition to the head-mounted cameras already described in FIG. 10. FIG. 12 illustrates head-mounted cameras 130 and 132 that measure larger regions 131 and 133 on the upper lip and the sides of the nose, respectively. And FIG. 13 illustrates head-mounted cameras 134 and 137 that measure regions 135 and 138 on the right and left cheeks and right and left sides of the mouth, respectively, in addition to the head-mounted cameras already described in FIG. 12.

In some embodiments, the head-mounted cameras may be physically coupled to the frame using a clip-on device configured to be attached/detached from a pair of eyeglasses in order to secure/release the device to/from the eyeglasses, multiple times. The clip-on device holds at least an inward-facing camera, a processor, a battery, and a wireless communication module. Most of the clip-on device may be located in front of the frame (as illustrated in FIG. 14b, FIG. 15b, and FIG. 18), or alternatively, most of the clip-on device may be located behind the frame, as illustrated in FIG. 17b and FIG. 16b.

FIG. 14a, FIG. 14b, and FIG. 14c illustrate two right and left clip-on devices 141 and 142, respectively, configured to attached/detached from an eyeglasses frame 140. The clip-on device 142 includes an inward-facing head-mounted camera 143 pointed at a region on the lower part of the face (such as the upper lip, mouth, nose, and/or cheek), an inward-facing head-mounted camera 144 pointed at the forehead, and other electronics 145 (such as a processor, a battery, and/or a wireless communication module). The clip-on devices 141 and 142 may include additional cameras illustrated in the drawings as black circles.

FIG. 15a and FIG. 15b illustrate a clip-on device 147 that includes an inward-facing head-mounted camera 148 pointed at a region on the lower part of the face (such as the nose), and an inward-facing head-mounted camera 149 pointed at the forehead. The other electronics (such as a processor, a battery, and/or a wireless communication module) is located inside the box 150, which also holds the cameras 148 and 149.

Figure 17A:
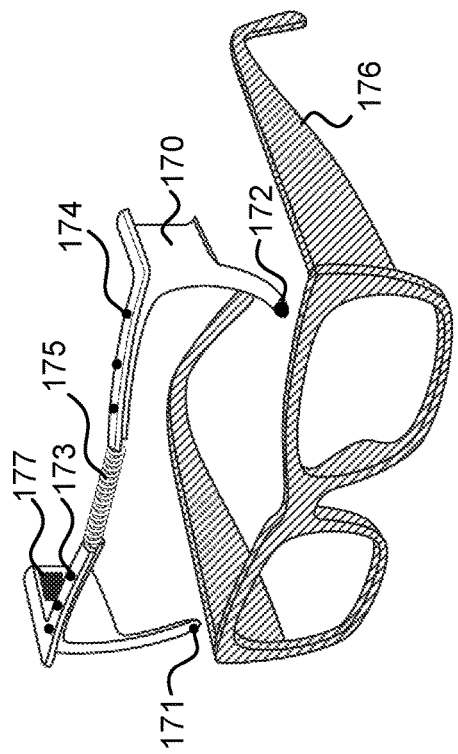
FIG. 17a and FIG. 17b illustrate embodiments of right and left clip-on devices that are configured to be attached behind an eyeglasses frame.
Figure 17B:
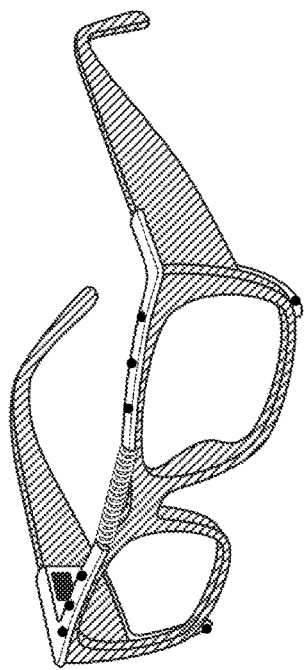
Figure 18:
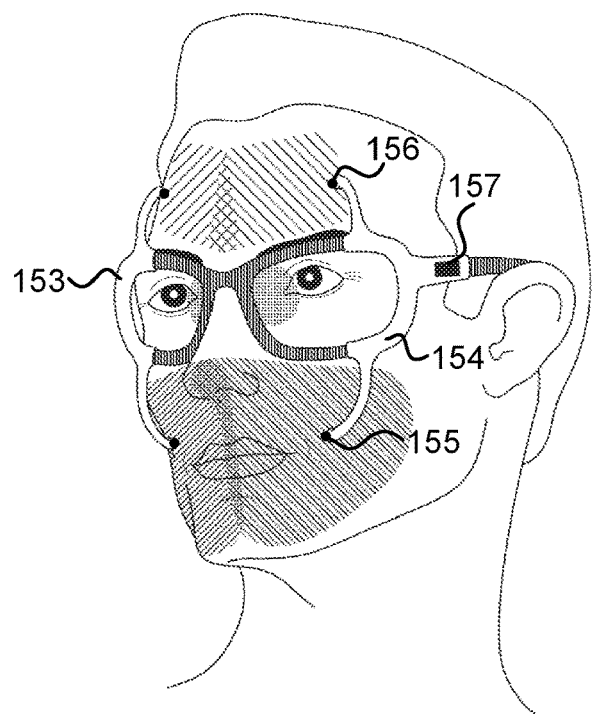
FIG. 18 illustrates embodiments of right and left clip-on devices, which are configured to be attached/detached from an eyeglasses frame, and have protruding arms to hold inward-facing head-mounted cameras.

FIG. 17a and FIG. 17b illustrate two right and left clip-on devices 160 and 161, respectively, configured to be attached behind an eyeglasses frame 165. The clip-on device 160 includes an inward-facing head-mounted camera 162 pointed at a region on the lower part of the face (such as the upper lip, mouth, nose, and/or cheek), an inward-facing head-mounted camera 163 pointed at the forehead, and other electronics 164 (such as a processor, a battery, and/or a wireless communication module). The clip-on devices 160 and 161 may include additional cameras illustrated in the drawings as black circles.

Figure 16A:
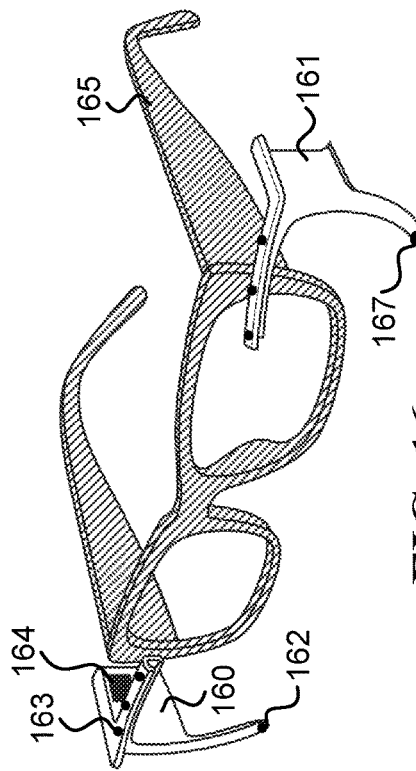
FIG. 16a and FIG. 16b illustrate an embodiment of a single-unit clip-on device that is configured to be attached behind an eyeglasses frame.
Figure 16B:
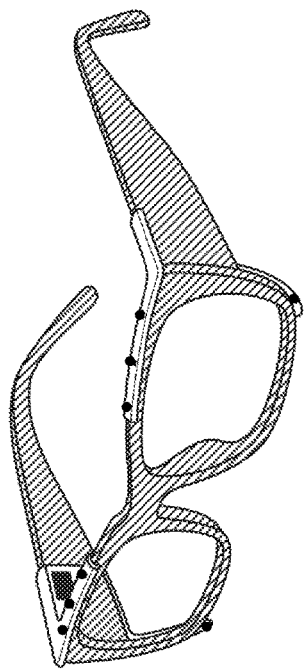

FIG. 16a and FIG. 16b illustrate a single-unit clip-on device 170, configured to be attached behind an eyeglasses frame 176. The single-unit clip-on device 170 includes inward-facing head-mounted cameras 171 and 172 pointed at regions on the lower part of the face (such as the upper lip, mouth, nose, and/or cheek), inward-facing head-mounted cameras 173 and 174 pointed at the forehead, a spring 175 configured to apply force that holds the clip-on device 170 to the frame 176, and other electronics 177 (such as a processor, a battery, and/or a wireless communication module). The clip-on device 170 may include additional cameras illustrated in the drawings as black circles.

FIG. 18 illustrates two right and left clip-on devices 153 and 154, respectively, configured to attached/detached from an eyeglasses frame, and having protruding arms to hold the inward-facing head-mounted cameras. Head-mounted camera 155 measures a region on the lower part of the face, head-mounted camera 156 measures regions on the forehead, and the left clip-on device 154 further includes other electronics 157 (such as a processor, a battery, and/or a wireless communication module). The clip-on devices 153 and 154 may include additional cameras illustrated in the drawings as black circles.

It is noted that the elliptic and other shapes of the ROIs in some of the drawings are just for illustration purposes, and the actual shapes of the ROIs are usually not as illustrated. It is possible to calculate the accurate shape of an ROI using various methods, such as a computerized simulation using a 3D model of the face and a model of a head-mounted system (HMS) to which a camera is physically coupled, or by placing a LED instead of the sensor, while maintaining the same field of view (FOV) and observing the illumination pattern on the face. Furthermore, illustrations and discussions of a camera represent one or more cameras, where each camera may have the same FOV and/or different FOVs. Unless indicated to the contrary, the cameras may include one or more sensing elements (pixels), even when multiple sensing elements do not explicitly appear in the figures; when a camera includes multiple sensing elements then the illustrated ROI usually refers to the total ROI captured by the camera, which is made of multiple regions that are respectively captured by the different sensing elements. The positions of the cameras in the figures are just for illustration, and the cameras may be placed at other positions on the HMS.

Sentences in the form of an "ROI on an area", such as ROI on the forehead or an ROI on the nose, refer to at least a portion of the area. Depending on the context, and especially when using a camera having a small number of pixels, the ROI may cover another area (in addition to the area). For example, a sentence in the form of "an ROI on the nose" may refer to either: 100% of the ROI is on the nose, or some of the ROI is on the nose and some of the ROI is on the upper lip.

The following is a description of embodiments of systems involving head-mounted cameras, which may be inward-facing or outward-facing cameras. An inward-facing head-mounted camera is a camera that captures images containing portions of a user's own face, while typically, an outward-facing camera will capture images that mostly do not include portions of the face. Captured images may be indicative of PATs at different regions. The PATs can be different at different regions of the body, due to the different distances of arterial pathways used by the blood to flow to the different regions, and difference in blood vessel characteristics (different diameters, elasticity, etc.). The difference between PATs at the different regions is utilized, in some embodiments, to calculate blood pressure values of the user.

In some embodiments, a system configured to calculate blood pressure of a user includes at least first and second head-mounted cameras (HCAMs), each configured to capture images of a region of interest (ROI) on the user's body. Herein, images of an ROI are denoted $IM_{ROI}$ and images of multiple ROIs may be denoted $IM_{ROIs}$. Optionally, each of the HCAMs is physically coupled to a frame worn on the user's head, such as an eyeglasses frame, or a frame of smartglasses or an extended reality device (i.e., an augmented realty device, a virtual reality device, and/or mixed reality device). The system also includes a computer that calculates a blood pressure value for the user based on imaging photoplethysmography (iPPG) signals recognizable in $IM_{ROIs}$ captured by HCAMs.

Some embodiments described herein typically rely on detecting PATs at multiple ROIs in order to calculate the blood pressure, where at least two of the ROIs are typically at least 5 cm away from each other, and/or the ROIs are on different body parts. Because of the distance between the ROIs and the fact that they may receive blood via different pathways, the changes observed due to an arrival of a pulse at a first ROI ($ROI_1$) may occur at a different time than changes observed due to the arrival of the pulse at a second ROI ($ROI_2$).

In one embodiment, the system that calculates blood pressure of a user includes a first inward-facing HCAM to capture images of a first ROI located on the face below the eyes and above the lips of the user (e.g., a maxillary process or the nose), and a second inward-facing HCAM to capture images of a second ROI comprising a portion of a temple and/or the forehead of the user. Optionally, at least one of the first and second HCAMs does not occlude its respective ROI. Optionally, both the first and second HCAMs do not occlude their respective ROIs. In one example, the center of the first ROI is located more than 6 cm away from the center of the second ROI, and changes in images of the first ROI due to a cardiac pulse wave occur at least 10 ms before, or at least 10 ms after, changes in images of the second ROI occur (due to the same cardiac pulse wave).

In one example, the second ROI comprises a portion of the right temple and/or the right side of the forehead, and the system includes a third inward-facing HCAM that captures images of a third ROI comprising a portion of the left temple and/or the left side forehead of the user. Optionally, the computer extracts from images of the third ROI an iPPG signal, and utilizes it to calculate the blood pressure value of the user (in addition to iPPG signals extracted from images taken with the other cameras).

Figure 20:
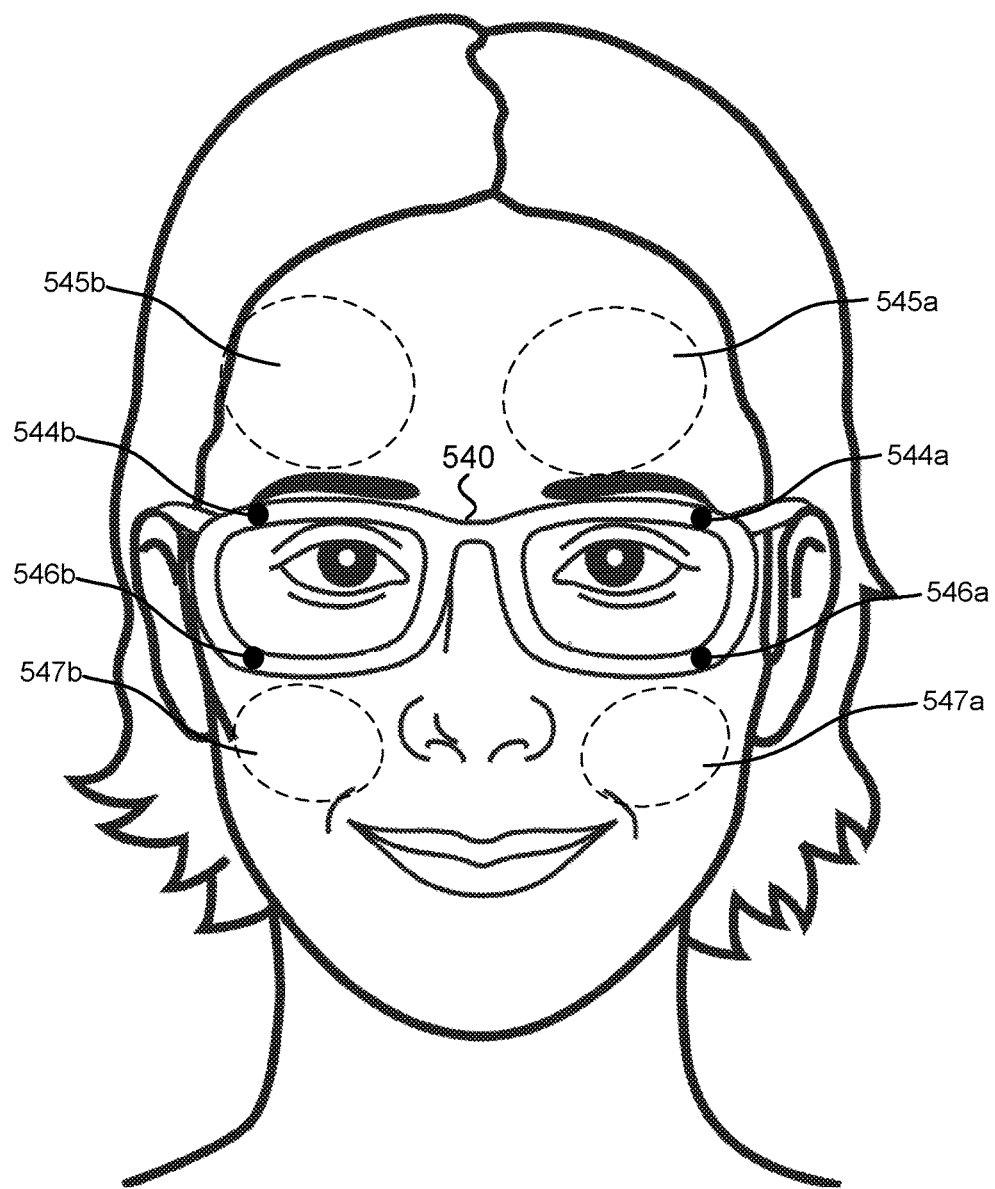
FIG. 20 illustrates an embodiment of a system configured to calculate blood pressure that includes at least two inward-facing HCAMs.

FIG. 20 illustrates one embodiment of a system configured to calculate blood pressure that includes at least two inward-facing HCAMs. The illustrated system includes frame 540, to which several HCAMs are coupled. These include inward-facing HCAMs 544a and 546a that are coupled to the left side of the frame 540 and are configured to capture images of ROIs 545a (portion left side of the forehead) and 547a (portion of left side maxillary process), respectively. Additionally, the illustrated system includes inward-facing HCAMs 544b and 546b that are coupled to the right side of the frame 540 and are configured to capture images of ROIs 545b (portion of right side of the forehead) and 547b (portion of right side maxillary process), respectively.

In another embodiment, the system that calculates blood pressure of a user includes an inward-facing HCAM to capture images of a first ROI that includes a portion of exposed skin of the user's face, and an outward-facing HCAM to capture images of a second ROI that includes exposed skin on a hand of the user (e.g., skin on the back of the hand, or skin on the palm of the hand). Optionally, the first ROI includes a portion of one or more of the following body parts of the user: a jaw, a cheek, a maxillary process, the nose, a skin around the eyes, a temple, and the forehead. Optionally, the second ROI comprises a portion of exposed skin located between the wrist and the fingertips. Optionally, at least one of the first and second HCAMs does not occlude its respective ROI. Optionally, both the first and second HCAMs do not occlude their respective ROIs.

In one example, the center of the first ROI is located more than 40 cm away from the center of the second ROI, when the hand is stretched to the side, and changes in images of the first ROI due to a cardiac pulse wave occur at least 20 ms before, or at least 20 ms after, changes in images of the second ROI occur (due to the same cardiac pulse wave).

Figure 21:
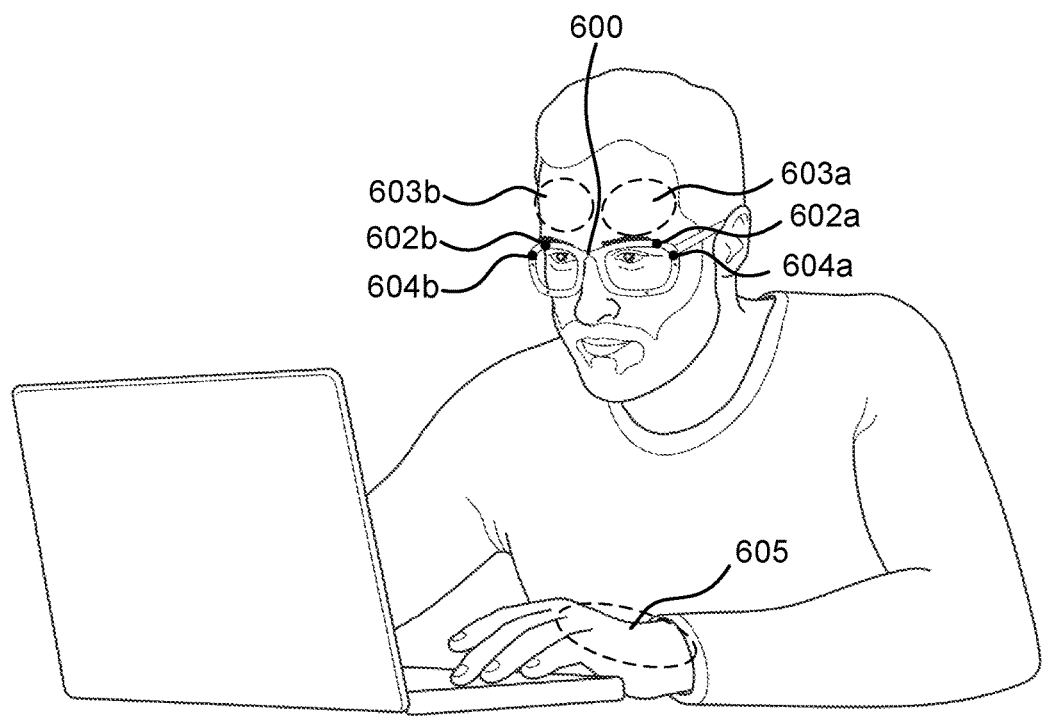
FIG. 21 illustrates one embodiment of a system configured to calculate blood pressure, which includes inward-facing HCAMs as well as outward-facing HCAMs.

FIG. 21 illustrates one embodiment of a system configured to calculate blood pressure, which includes inward-facing HCAMs as well as outward-facing HCAMs. The illustrated system includes frame 600, to which several HCAMs are coupled. These include inward-facing HCAMs 602a and 602b that are configured to capture images of ROIs 603a and 603b (portions of left and right sides of the forehead, respectively). Additionally, the illustrated system includes outward-facing HCAMs 604a and 604b. In the illustration, at least one of HCAMs 604a and 604b captures images that include the user's hand (ROI 605).

As opposed the ROIs on the face, which typically do not change their position with respect to an inward-facing HCAM, an ROI that includes a portion of the hand may change its position in $IM_{ROI}$ (due to movements of the head and/or hand), and may not appear in certain images at all. Thus, in some embodiments, to detect what portions of $IM_{ROI}$ include exposed skin located between the wrist and the fingertips (e.g., palm or back of hand), and/or whether an image includes portions of the user's hand, the computer may utilize various image detection algorithms known in the art. Some examples of algorithmic approaches that may be utilized are described in Kölsch et al., "Robust Hand Detection." FGR. 2004, which describe hand detection using a variant of the recognition method of Viola and Jones. Another approach to hand detection is given by Mittal et al., "Hand detection using multiple proposals", BMVC, 2011, which describe a two-stage method for detecting hands and their orientation in unconstrained images. Additional methods for detecting hands in images are reviewed in Erol et al., "Vision-based hand pose estimation: A review", Computer Vision and Image Understanding 108.1-2 (2007): 52-73.

It is to be noted that while the majority of algorithms for detecting hands in images are utilized with images from cameras that are not head-mounted, the described algorithmic approaches can work equally well for images from HCAMs, and/or be easily modified by one skilled in the art to detect hands in $IM_{ROI}$. For algorithms that utilize machine learning methods, adapting algorithms for detection of hands to handle data from HCAMs may simply involve collection of training data that includes $IM_{ROI}$ and annotations of the hands therein.

HCAMs utilized in embodiments described herein are typically small and lightweight. In some embodiments, an HCAM weighs below 10 g, or less than 2 g, and is physically coupled to a frame configured to be worn on the user's head (e.g., a frame of glasses or and augmented reality headset). The frame is configured to hold HCAM less than 10 cm from the user's head. HCAM may involve various types of sensors (sensing elements). In one example, HCAM is a video camera that includes multiple CMOS or CCD pixels. HCAMs may capture images at various rates. In one example, the images taken by HCAM are captured at a frame rate of at least 30 frames per second (fps). In another example, the images are captured at a frame rate of at least 100 fps. In still another example, the images are captured at a frame rate of at least 256 fps. In another embodiment, HCAM is an angle-sensitive pixel sensor camera, weighing less than 1 g. Some examples of angle-sensitive pixel sensor cameras are described in US Patent Applications 2017/0112376 and 2018/0031372, and in other publications by Dr. Albert Wang and Dr. Patrick Gill.

In some embodiments, HCAM may capture light in the near infrared spectrum (NIR). Optionally, HCAM may include optics and sensors that capture light rays in at least one of the following NIR spectrum intervals: 700-800 nm, 700-900 nm, or 700-1,000 nm. Optionally, the computer may utilize data obtained in a NIR spectrum interval to calculate the blood pressure (in addition to, or instead of, data obtained from the visible spectrum). Optionally, the sensors may be CCD sensors and/or CMOS sensors designed to be sensitive in the NIR spectrum.

In some embodiments, the system may include an optical emitter configured to direct electromagnetic radiation at the ROI. Optionally, the optical emitter comprises one or more of the following: a laser diode (LD), a light-emitting diodes (LED), and an organic light-emitting diode (OLED).

It is to be noted that when embodiments described in this disclosure utilize optical emitters directed at a region of interest (ROI), the optical emitter may be positioned in various locations relative to the ROI. In some embodiments, the optical emitter may be positioned essentially directly above the ROI, such that electromagnetic radiation is emitted at an angle that is perpendicular (or within 10 degrees from being perpendicular) relative to the ROI. Optionally, a camera may be positioned near the optical emitter in order to capture the reflection of electromagnetic radiation from the ROI. In other embodiments, the optical emitter may be positioned such that it is not perpendicular to the ROI, and optionally does not occlude the ROI. In one example, the optical emitter may be located at the top of a frame of a pair of eyeglasses, and the ROI may include a portion of the forehead. In another example, the optical emitter may be located on an arm of a frame of a pair of eyeglasses, and the ROI may be located above or below the arm.

Due to the proximity of HCAM to the face, in some embodiments, there may be an acute angle between the optical axis of HCAM and the ROI (e.g., when the ROI includes a region on the forehead). In order to improve the sharpness of $IM_{ROI}$, HCAM may be configured to operate in a way that takes advantage of the Scheimpflug principle. In one embodiment, HCAM includes a sensor and a lens; the sensor plane is tilted by a fixed angle greater than 2° relative to the lens plane according to the Scheimpflug principle in order to capture a sharper image when HCAM is worn by the user (where the lens plane refers to a plane that is perpendicular to the optical axis of the lens, which may include one or more lenses). Optionally, HCAM does not occlude the ROI. In another embodiment, HCAM includes a sensor, a lens, and a motor; the motor tilts the lens relative to the sensor according to the Scheimpflug principle. The tilt improves the sharpness of $IM_{ROI}$ when HCAM is worn by the user. Additional details regarding the application of the Scheimpflug principle are discussed further below.

Variations in the reflected ambient light may introduce artifacts into images collected with HCAMs, which can add noise to an iPPG signal extracted from the images. In some embodiments, the system includes an outward-facing HCAM, which is worn on the user's head, and takes images of the environment ($IM_{ENV}$). Optionally, this outward-facing HCAM is located less than 10 cm from the user's face and weighs below 10 g, or below 2 g. Optionally, the outward-facing HCAM may include optics that provide it with a wide field of view. Optionally, the computer calculates the blood pressure based on both $IM_{ROI}$ and $IM_{ENV}$. In one example, given that $IM_{ENV}$ is indicative of illumination towards the face and $IM_{ROI}$ is indicative of reflections from the face, utilizing $IM_{ENV}$ can account, at least in part, for variations in ambient light that, when left unaccounted, may possibly lead, in some embodiments, to image artifacts that can lead to less accurate calculations.

The computer is configured, in some embodiments, to calculate a blood pressure value for the user based on iPPG signals recognizable in $IM_{ROIs}$ captured by HCAMs (e.g., the first and second HCAMs in one of the embodiments described above). Examples of computers that may be utilized to perform this calculation are computer 400 or computer 410 illustrated in FIG. 22a and FIG. 22b, respectively. Herein, sentences of the form "iPPG signal recognizable in $IM_{ROI}$" refer to effects of blood volume changes due to pulse waves that may be extracted from a series of images of an ROI. These changes may be identified and/or utilized by a computer (e.g., in order to generate a signal indicative of the blood volume at the ROI), but need not necessarily be recognizable to the naked eye (e.g., because of their subtlety, the short duration in which they occur, or involvement of light outside of the visible spectrum).

In some embodiments, the blood pressure calculated by the computer may refer to one or more of the following values: the systolic blood pressure of the user, the diastolic blood pressure of the user, and the mean arterial pressure (MAP) of the user. The computer may employ various approaches for calculating the blood pressure, as explained in further detail in embodiments described below.

The computer may utilize various preprocessing approaches to assist in calculations and/or in extraction of an iPPG signal from $IM_{ROI}$. Optionally, $IM_{ROI}$ may undergo various preprocessing steps prior to being used by the computer to detect the physiological response, and/or as part of the process of the detection of the physiological response. Some non-limiting examples of the preprocessing include: normalization of pixel intensities (e.g., to obtain a zero-mean unit variance time series signal), and conditioning a time series signal by constructing a square wave, a sine wave, or a user defined shape, such as that obtained from an ECG signal or a PPG signal as described in U.S. Pat. No. 8,617,081. Additionally or alternatively, images may undergo various preprocessing to improve the signal, such as color space transformation (e.g., transforming RGB images into a monochromatic color or images in a different color space), blind source separation using algorithms such as independent component analysis (ICA) or principal component analysis (PCA), and various filtering techniques, such as detrending, bandpass filtering, and/or continuous wavelet transform (CWT). Various preprocessing techniques known in the art that may assist in extracting an iPPG signal from $IM_{ROI}$ are discussed in Zaunseder et al. (2018), "Cardiovascular assessment by imaging photoplethysmography-a review", Biomedical Engineering 63(5), 617-634. An example of preprocessing that may be used in some embodiments is given in U.S. Pat. No. 9,020,185, titled "Systems and methods for non-contact heart rate sensing", which describes how a times-series signals obtained from video of a user can be filtered and processed to separate an underlying pulsing signal by, for example, using an ICA algorithm.

Calculating the blood pressure may be done in various approaches. In one example, iPPG signals are extracted from $IM_{ROIs}$ and utilized to directly calculate PATs at different ROIs. Optionally, a PAT calculated from an iPPG signal represents a time at which the value representing blood volume (in the waveform represented in the iPPG) begins to rise (signaling the arrival of the pulse). Alternatively, the PAT may be calculated as a different time, with respect to the waveform, such as the time at which a value representing blood volume reaches a maximum or a certain threshold, or the PAT may be the average of the time the blood volume is above a certain threshold. Another approach that may be utilized to calculate the PAT from an iPPG is described in Sola et al. "Parametric estimation of pulse arrival time: a robust approach to pulse wave velocity", Physiological measurement 30.7 (2009): 603, which describe a family of PAT estimators based on the parametric modeling of the anacrotic phase of a pressure pulse.

It is to be noted that while the prior art approaches involve analysis of video obtained from cameras that are not head-mounted, and are typically more distant from their ROI than the inward-facing HCAMs herein, and are possibly at different orientations relative to the ROI, the computational approaches described in the prior art used to detect pulse wave arrivals can be readily adapted by one skilled in the art to handle $IM_{ROI}$. In some cases, embodiments described herein may provide video in which a desired signal is more easily detectable compared to some of the prior art approaches. For example, given the typically short distance from an inward-facing HCAM to the ROI, the ROI is expected to cover a larger portion of the images in $IM_{ROI}$ compared to images obtained by video cameras in some of the prior art references. Additionally, due to the proximity of an inward-facing HCAM to the ROI, additional illumination that is required in some prior art approaches, such as illuminating the skin for a pulse oximeter to obtain a photoplethysmographic (PPG) signal, may not be needed. Furthermore, given an inward-facing HCAM's fixed location and orientation relative to the ROI (even when the user makes lateral and/or angular movements), many pre-processing steps that need to be implemented by the prior art approaches, such as image registration and/or face tracking, are extremely simplified in some of the embodiments described herein, or may be foregone altogether.

Calculating the blood pressure may be done in different ways, in different embodiments. In some embodiments, the blood pressure may be calculated based on a difference in PATs at different ROIs. In one example, first and second ROIs, denoted $ROI_1$ and $ROI_2$, are imaged using respective $HCAM_1$ and $HCAM_2$, to obtain $IM_{ROI1}$ and $IM_{ROI2}$, respectively. Using various processing approaches described above, the computer extracts two iPPG signals (denoted $iPPG_1$ and $iPPG_2$) from $IM_{ROI1}$ and $IM_{ROI2}$, respectively. The PATs are extracted from $iPPG_1$ and $iPPG_2$. The difference $\Delta t = t_1 - t_2$, between $t_1$ (a PAT at $ROI_1$) and $t_2$ (a PAT at $ROI_2$), can be utilized directly to calculate the blood pressure. The calculation of the blood pressure relies on the fact that the magnitude of $\Delta t$ is inversely proportional to the pulse wave velocity (that is directly correlated to the blood pressure). Thus, a smaller $\Delta t$ corresponds to a larger blood pressure value. In one example, the transformation from $\Delta t$ to a blood pressure value is a linear transformation of the form BP=a/Δt+b (where a and b are fixed parameters). In other examples, a nonlinear transformation may be utilized to convert Δt to a blood pressure value.

In some embodiments, due the each person's unique layout of the circulatory system, it might not be accurate to directly convert Δt to blood pressure value with fixed, general parameters (e.g., use the same parameters for different users). Optionally, in order to improve accuracy of blood pressure calculations, the computer may utilize calibration values that can help account for a user's specific circulatory system characteristics. Optionally, calibration values include measurements of the user's blood pressure, taken by a different device (e.g., a cuff-based blood pressure monitoring system). These measurements, along with the Δt values calculated from iPPG signals taken at the same time the blood pressure measurements were taken, can be used to calculate parameters, such as coefficients of linear or non-linear transformations between Δt and blood pressure values. These parameters can then be used by the computer to calculate a blood pressure for a user, given Δt calculated based on PATs detected in iPPG signals of the user (e.g., $iPPG_1$ and $iPPG_2$ mentioned above). Optionally, the parameters are calculated based on multiple calibration measurements that include PATs detected at different times, when the user's blood pressure had different values.

In another approach, the computer may utilize machine learning methods to calculate the blood pressure from $IM_{ROIs}$ captured by HCAMs. In some embodiments, the computer calculates feature values based on data comprising $IM_{ROIs}$ (e.g., $IM_{ROI1}$ and $IM_{ROI2}$ of one of the embodiments mentioned above) and utilizes a model to calculate, based on the feature values, the blood pressure value of the user. The following are some examples of the various types of feature values that may be generated based on $IM_{ROIs}$ by the computer.

In one embodiment, at least some of the feature values may be derived directly from values of pixels in $IM_{ROI}$. Optionally, at least some of the feature values are values of pixels from the $IM_{ROIs}$. Optionally, one or more of the feature values may be the values of the pixels themselves or some simple function of the pixels, such as the average of pixels at certain regions in each of the images. Optionally, one or more of the feature values may be various low-level features derived from images, such as features generated using Gabor filters, local binary patterns (LBP) and their derivatives, algorithms such as SIFT and/or SURF (and their derivatives), image keypoints, histograms of oriented gradients (HOG) descriptors, and products of statistical procedures such independent component analysis (ICA), principal component analysis (PCA), or linear discriminant analysis (LDA). Optionally, one or more of the feature values may derived from multiple images taken at different times, such as volume local binary patterns (VLBP), cuboids, and/or optical strain-based features. In one example, one or more of the feature values may represent a difference between values of pixels at one time t at a certain ROI and values of pixels at a different ROI at some other time t+x (which can help detect different arrival times of a pulse wave).

In some embodiments, at least some of the feature values are generated based on iPPG signals extracted from $IM_{ROIs}$. Optionally, the feature values indicate PATs at different ROIs, and/or a difference in PATs at different ROIs (e.g., a feature value may be indicative of Δt described above). In one example, feature values are generated based on $iPPG_1$ and $iPPG_2$, which are indicative of PATs at $ROI_1$ and $ROI_2$, respectively. In this example, the computer generates a feature value, based on the PATs, which is indicative of the difference between when a pulse wave is manifested in $IM_{ROI1}$ and $IM_{ROI2}$. In another example, one or more of the feature values may be indicative of the shape and/or other characteristics of a pulse wave, as indicated in an iPPG signal extracted from $IM_{ROI}$. For example, feature values derived from an iPPG signal may indicate one or more of the following: magnitude of a systolic peak, magnitude of a diastolic peak, duration of the systolic phase, and duration of the diastolic phase.

In some embodiments, at least some of the feature values may represent calibration values of a user. For example, at least some of the feature values are indicative of a difference in PATs between different ROIs when certain blood pressure values were measured (e.g., using a different reference device such as a cuff-based blood pressure monitor). In one example, the computer extracts iPPG signals, denoted $iPPG_1$ and $iPPG_2$, from images of two ROIs, denoted $IM_{ROI1}$ and $IM_{ROI2}$, respectively. $iPPG_1$ and $iPPG_2$ are indicative of pulse arrival times at the first and second regions of interest, respectively. In this example, the computer generates one or more values that are indicative of: (i) a certain blood pressure value of the user that was measured during a certain previous period, and (ii) a difference between when pulse waves of the user, as manifested in $IM_{ROI1}$ and $IM_{ROI2}$ that were taken during the certain previous period. In another example, at least some of the feature values may represent measured blood pressure for various differences in PATs between ROIs.

In some embodiments, one or more of the feature values may be generated based on additional inputs from sources other than HCAMs. Optionally, these one or more feature values may assist in calculation of more accurate blood pressure values and/or with accounting for factors that can influence the user's blood pressure.

Stress is a factor that can influence the diameter of the arteries, and thus influence the value of the calculated blood pressure. In one embodiment, the computer is further configured to: receive a value indicative of a stress level of the user, and generate at least one of the feature values based on the received value. Optionally, the value indicative of the stress level is obtained using a thermal camera. In one example, the system may include an inward-facing head-mounted thermal camera configured to take measurements of a periorbital region of the user, where the measurements of a periorbital region of the user are indicative of the stress level of the user. In another example, the system includes an inward-facing head-mounted thermal camera configured to take measurements of a region on the forehead of the user, where the measurements of the region on the forehead of the user are indicative of the stress level of the user. In still another example, the system includes an inward-facing head-mounted thermal camera configured to take measurements of a region on the nose of the user, where the measurements of the region on the nose of the user are indicative of the stress level of the user.

Hydration is a factor that affects blood viscosity, which can affect the speed at which blood flows in the body, and consequently affect blood pressure calculated based on PATs. In one embodiment, the computer is further configured to: receive a value indicative of a hydration level of the user, and generate at least one of the feature values based on the received value. Optionally, the system includes an additional camera configured to detect intensity of radiation that is reflected from a region of exposed skin of the user, where the radiation is in spectral wavelengths chosen to be preferentially absorbed by tissue water. In one example, said wavelengths are chosen from three primary bands of wavelengths of approximately 1100-1350 nm, approximately 1500-1800 nm, and approximately 2000-2300 nm. Optionally, measurements of the additional camera are utilized by the computer as values indicative of the hydration level of the user.

The following are examples of embodiments that utilize additional inputs to generate feature values used to calculate blood pressure. In one embodiment, the computer is configured to: receive a value indicative of a temperature of the user's body, and generate at least one of the feature values based on the received value. In another embodiment, the computer is configured to: receive a value indicative of a movement of the user's body, and generate at least one of the feature values based on the received value. For example, the computer may receive the input form an accelerometer in a mobile device carried by the user. In yet another embodiment, the computer is configured to: receive a value indicative of an orientation of the user's head, and generate at least one of the feature values based on the received value. For example, the computer may receive the values indicative of the head's orientation from a gyroscope. In still another embodiment, the computer is configured to: receive a value indicative of consumption of a substance by the user, and generate at least one of the feature values based on the received value. Optionally, the substance comprises one or more of the following: a vasodilator, a vasoconstrictor.

The model utilized to calculate the blood pressure values of the user may be generated based on training data comprising: previous $IM_{ROIs}$ (e.g., $IM_{ROI1}$ and $IM_{ROI2}$ from one of the embodiments above) and blood pressure values corresponding to times at which the previous $IM_{ROIs}$ were taken. This data is used to generate samples, each sample including feature values generated based on some of the previously taken $IM_{ROI}$ that were taken during a certain period, and a label generated based on a blood pressure value, which corresponds to the certain period (e.g., it was taken during the certain period, and/or shortly before and/or after the certain period, such as within five minutes from the certain period).

The model may be generated based on data of the user and/or data of other users. In some embodiments, the previously taken $IM_{ROIs}$ comprise images of body parts of the user, and the blood pressure values corresponding to the previously taken $IM_{ROIs}$ are blood pressure values of the user measured using a device that does not utilize HCAMs (e.g., a cuff-based blood pressure monitor). In other embodiments, the previously taken $IM_{ROIs}$ comprise images of body parts of other users, and the blood pressure values corresponding to the previously taken $IM_{ROIs}$ are blood pressure values of the other users, measured using one or more devices that do not utilize HCAMs.

In order to achieve a robust model, which may be useful for calculating blood pressure of a user in various conditions, in some embodiments, the samples used in the training may include samples based on $IM_{ROIs}$ taken in different conditions. Optionally, the samples are generated based on $IM_{ROIs}$ taken on different days. In a first example, the system does not occlude the ROIs, and the model is trained on samples generated from a first set of $IM_{ROIs}$ taken while the user was indoors and not in direct sunlight, and is also trained on other samples generated from a second set of $IM_{ROIs}$ taken while the user was outdoors, in direct sunlight. In a second example, the model is trained on samples generated from a first set of $IM_{ROIs}$ taken during daytime, and is also trained on other samples generated from a second set of $IM_{ROIs}$ taken during nighttime. In a third example, the model is trained on samples generated from a first set of $IM_{ROIs}$ taken while the user was exercising and moving, and is also trained on other samples generated from a second set of $IM_{ROIs}$ taken while the user was sitting and not exercising. And a fourth example, the model is trained on samples generated from a first set of $IM_{ROIs}$ taken less than 30 minutes after the user had an alcoholic beverage, and is also trained on other samples generated from a second set of $IM_{ROIs}$ taken on a day in which the user did not have an alcoholic beverage.

Utilizing the model to calculate the blood pressure model may involve the computer performing various operations, depending on the type of model. The following are some examples of various possibilities for the model, and the type of calculations that may be accordingly performed by a computer, in some embodiments, in order to calculate the blood pressure: (a) the model comprises parameters of a decision tree. Optionally, the computer simulates a traversal along a path in the decision tree, determining which branches to take based on the feature values. A value indicative of the blood pressure may be obtained at the leaf node and/or based on calculations involving values on nodes and/or edges along the path; (b) the model comprises parameters of a regression model (e.g., regression coefficients in a linear regression model or a logistic regression model). Optionally, the computer multiplies the feature values (which may be considered a regressor) with the parameters of the regression model in order to obtain the value indicative of the blood pressure; and/or (c) the model comprises parameters of a neural network. For example, the parameters may include values defining at least the following: (i) an interconnection pattern between different layers of neurons, (ii) weights of the interconnections, and (iii) activation functions that convert each neuron's weighted input to its output activation. Optionally, the computer provides the feature values as inputs to the neural network, computes the values of the various activation functions and propagates values between layers, and obtains an output from the network, which is the value indicative of the blood pressure.

In some embodiments, a machine learning approach that may be applied to calculating the blood pressure based on $IM_{ROIs}$ may be characterized as "deep learning". In one embodiment, the model may include parameters describing multiple hidden layers of a neural network. Optionally, the model may include a convolution neural network (CNN). In one example, the CNN may be utilized to identify certain patterns in the video images, such as the patterns of corresponding to blood volume effects and ballistocardiographic effects of the cardiac pulse. Due to the fact that calculating the blood pressure may be based on multiple, possibly successive, images that display a certain pattern of change over time (i.e., across multiple frames), these calculations may involve retaining state information that is based on previous images. Optionally, the model may include parameters that describe an architecture that supports such a capability. In one example, the model may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

In order to improve the accuracy of blood pressure calculations, and in some cases in order to better account for interferences, in some embodiments, the computer may utilize $IM_{ROIs}$ captured by more than two HCAMs. Utilizing images from more than two ROIs may confer several advantages. First, calculating more than two PATs can give a larger number of differences between PATs (i.e., multiple Δt values), which can help to address issues involving noisy measurements (e.g., due to movement or environmental artifacts). However, having more than two PATs can also help account for different factors that may influence the speed at which a pulse wave travels.

The speed of blood propagating through the arteries, and therefore also the blood pressure calculated based on that value, is affected by multiple factors, such as the cardiac output, the vessel compliance, vessel diameter, vessel length, and blood viscosity. Some of these factors, such as cardiac output (at a given time) can change very quickly, while others, such as vessel length can change very slowly (over a course of years). Blood viscosity is a factor that can change throughout the day (e.g., due to hydration levels). Another factor mentioned above that can influence the velocity of the arterial blood flow is the diameter of the arteries. This value can change in certain circumstances, such as a result of stress (e.g., due to the release of stress hormones), or due to consumption of substances that cause arterial dilation. Thus, there is more than one varying factor that can influence blood pressure. Since different arteries at different locations have different properties (e.g., different thickness and elasticity), they may be affected differently by these factors; therefore, utilizing PATs at multiple ROIs can help better account for these factors and increase accuracy of blood pressure calculations.

Various embodiments described herein involve calculation of blood pressure based on $IM_{ROIs}$ using machine learning methods. Herein, "machine learning" methods refers to learning from examples using one or more approaches. Examples of machine learning approaches include: decision tree learning, association rule learning, regression models, nearest neighbors classifiers, artificial neural networks, deep learning, inductive logic programming, support vector machines, clustering, Bayesian networks, reinforcement learning, representation learning, similarity and metric learning, sparse dictionary learning, genetic algorithms, rule-based machine learning, and/or learning classifier systems.

Herein, a "machine learning-based model" is a model trained using machine learning methods. For brevity's sake, at times, a "machine learning-based model" may simply be called a "model". Referring to a model as being "machine learning-based" is intended to indicate that the model is trained using machine learning methods (otherwise, "model" may also refer to a model generated by methods other than machine learning).

Herein, feature values may be considered input to a computer that utilizes a model to perform the calculation of a value, such as a value indicative of the blood pressure of a user. It is to be noted that the terms "feature" and "feature value" may be used interchangeably when the context of their use is clear. However, a "feature" typically refers to a certain type of value, and represents a property, while "feature value" is the value of the property with a certain instance (sample).

It is to be noted that when it is stated that feature values are generated based on data comprising multiple sources, it means that for each source, there is at least one feature value that is generated based on that source (and possibly other data). For example, stating that feature values are generated from $IM_{ROI}$ of first and second ROIs ($IM_{ROI1}$ and $IM_{ROI2}$, respectively) means that the feature values may include a first feature value generated based on $IM_{ROI1}$ and a second feature value generated based on $IM_{ROI2}$.

In addition to feature values that are generated based on $IM_{ROIs}$, in some embodiments, at least some feature values utilized by a computer (e.g., to calculate blood pressure or train a model) may be generated based on additional sources of data. Some examples of the additional sources include: (i) measurements of the environment such as temperature, humidity level, noise level, elevation, air quality, a wind speed, precipitation, and infrared radiation; (ii) contextual information such as the time of day (e.g., to account for effects of the circadian rhythm), day of month (e.g., to account for effects of the lunar rhythm), day in the year (e.g., to account for seasonal effects), and/or stage in a menstrual cycle; (iii) information about the user being measured such as sex, age, weight, height, and/or body build. Alternatively or additionally, at least some feature values may be generated based on physiological signals of the user obtained by sensors that are not HCAMs, such as a photoplethysmogram (PPG) sensor, an electrocardiogram (ECG) sensor, an electroencephalography (EEG) sensor, a galvanic skin response (GSR) sensor, or a thermistor.

A machine learning-based model used to calculate blood pressure may be trained, in some embodiments, based on data collected in day-to-day, real world scenarios. As such, the data may be collected at different times of the day, while users perform various activities, and in various environmental conditions. Utilizing such diverse training data may enable a trained model to be more resilient to the various effects different conditions can have on $IM_{ROIs}$, and consequently, be able to achieve better detection of the blood pressure in real world day-to-day scenarios.

Normally, the lens plane and the sensor plane of a camera are parallel, and the plane of focus (PoF) is parallel to the lens and sensor planes. If a planar object is also parallel to the sensor plane, it can coincide with the PoF, and the entire object can be captured sharply. If the lens plane is tilted (not parallel) relative to the sensor plane, it will be in focus along a line where it intersects the PoF. The Scheimpflug principle is a known geometric rule that describes the orientation of the plane of focus of a camera when the lens plane is tilted relative to the sensor plane.

Figure 19A:
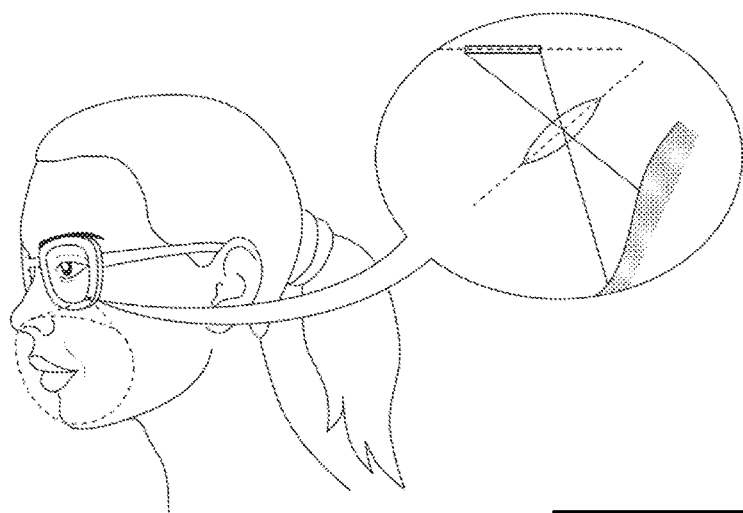
FIG. 19a is a schematic illustration of an inward-facing head-mounted camera embedded in an eyeglasses frame, which utilizes the Scheimpflug principle.

FIG. 19a is a schematic illustration of an inward-facing head-mounted camera 550 embedded in an eyeglasses frame 551, which utilizes the Scheimpflug principle to improve the sharpness of the image taken by the camera 550. The camera 550 includes a sensor 558 and a lens 555. The tilt of the lens 555 relative to sensor 558, which may also be considered as the angle between the lens plane 555 and the sensor plane 559, is determined according to the expected position of the camera 550 relative to the ROI 552 when the user wears the eyeglasses. For a refractive optical lens, the "lens plane" 556 refers to a plane that is perpendicular to the optical axis of the lens 555. Herein, the singular also includes the plural, and the term "lens" refers to one or more lenses. When "lens" refers to multiple lenses (which is usually the case in most modern cameras having a lens module with multiple lenses), then the "lens plane" refers to a plane that is perpendicular to the optical axis of the lens module.

Figure 19B:
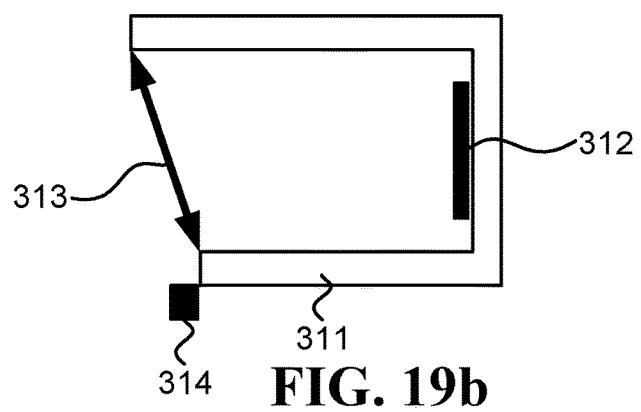
FIG. 19b is a schematic illustration of a camera that is able to change the relative tilt between its lens and sensor planes according to the Scheimpflug principle.

The Scheimpflug principle may be used for both thermal cameras (based on lenses and sensors for wavelengths longer than 2500 nm) and visible-light and/or near-IR cameras (based on lenses and sensors for wavelengths between 400-900 nm). FIG. 19b is a schematic illustration of a camera that is able to change the relative tilt between its lens and sensor planes according to the Scheimpflug principle.

Housing 311 mounts a sensor 312 and lens 313. The lens 313 is tilted relative to the sensor 312. The tilt may be fixed according to the expected position of the camera relative to the ROI when the user wears the HMS, or may be adjusted using motor 314. The motor 314 may move the lens 313 and/or the sensor 312.

In one embodiment, an HMS device includes a frame configured to be worn on a user's head, and an inward-facing camera physically coupled to the frame. The inward-facing camera may assume one of two configurations: (i) the inward-facing camera is oriented such that the optical axis of the camera is above the Frankfort horizontal plane and pointed upward to capture an image of a region of interest (ROI) above the user's eyes, or (ii) the inward-facing camera is oriented such that the optical axis is below the Frankfort horizontal plane and pointed downward to capture an image of an ROI below the user's eyes. The inward-facing camera includes a sensor and a lens. The sensor plane is tilted by more than 2° relative to the lens plane according to the Scheimpflug principle in order to capture a sharper image.

In another embodiment, an HMS includes an inward-facing head-mounted camera that captures an image of an ROI on a user's face, when worn on the user's head. The ROI is on the user's forehead, nose, upper lip, cheek, and/or lips. The camera includes a sensor and a lens. And the sensor plane is tilted by more than 2° relative to the lens plane according to the Scheimpflug principle in order to capture a sharper image.

Because the face is not planar and the inward-facing head-mounted camera is located close to the face, an image captured by a camera having a wide field of view (FOV) and a low f-number may not be perfectly sharp, even after applying the Scheimpflug principle. Therefore, in some embodiments, the tilt between the lens plane and the sensor plane is selected such as to adjust the sharpness of the various areas covered in the ROI according to their importance for detecting the user's physiological signals. In one embodiment, the ROI covers first and second areas, where the first area includes finer details and/or is more important for detecting the physiological signals than the second area. Therefore, the tilt between the lens and sensor planes is adjusted such that the image of the first area is shaper than the image of the second area.

In one embodiment, the tilt between the lens plane and sensor plane is fixed. The fixed tilt is selected according to an expected orientation between the camera and the ROI when a user wears the frame. Having a fixed tilt between the lens and sensor planes may eliminate the need for an adjustable electromechanical tilting mechanism. As a result, a fixed tilt may reduce the weight and cost of the camera, while still providing a sharper image than an image that would be obtained from a similar camera in which the lens and sensor planes are parallel. The magnitude of the fixed tilt may be selected according to facial dimensions of an average user expected to wear the system, or according to a model of the specific user expected to wear the system in order to obtain the sharpest image.

In another embodiment, the system includes an adjustable electromechanical tilting mechanism configured to change the tilt between the lens and sensor planes according to the Scheimpflug principle based on the orientation between the camera and the ROI when the frame is worn by the user. The tilt may be achieved using at least one motor, such as a brushless DC motor, a stepper motor (without a feedback sensor), a brushed DC electric motor, a piezoelectric motor, and/or a micro-motion motor.

The adjustable electromechanical tilting mechanism configured to change the tilt between the lens and sensor planes may include one or more of the following mechanisms: (i) a mirror that changes its angle; (ii) a device that changes the angle of the lens relative to the sensor; and/or (iii) a device that changes the angle of the sensor relative to the lens. In one embodiment, the camera, including the adjustable electromechanical tilting mechanism, weighs less than 10 g, and the adjustable electromechanical tilting mechanism is able to change the tilt in a limited range below 30° between the two utmost orientations between the lens and sensor planes. Optionally, the adjustable electromechanical tilting mechanism is able to change the tilt in a limited range below 20° between the two utmost orientations between the lens and sensor planes. In another embodiment, the adjustable electromechanical tilting mechanism is able to change the tilt in a limited range below 10°. In some embodiments, being able to change the tilt in a limited range reduces at least one of the weight, cost, and size of the camera, which is advantageous for a wearable device. In one example, the camera is manufactured with a fixed predetermined tilt between the lens and sensor planes, which is in addition to the tilt provided by the adjustable electromechanical tilting mechanism. The fixed predetermined orientation may be determined according to the expected orientation between the camera and the ROI for an average user, such that the adjustable electromechanical tilting mechanism is used to fine-tune the tilt between the lens and sensor planes for the specific user who wears the frame and has facial dimensions that are different from the average user.

Various embodiments described herein involve an HMS that may be connected, using wires and/or wirelessly, with a device carried by the user and/or a non-wearable device. The HMS may include a battery, a computer, sensors, and a transceiver.

Figure 22A:
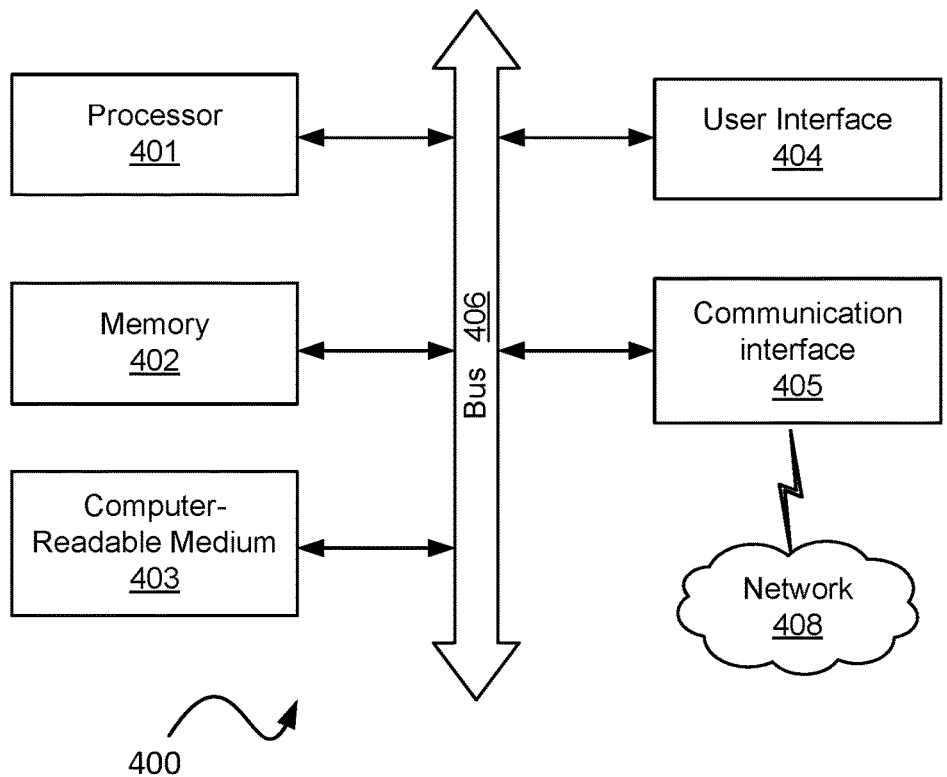
FIG. 22a and FIG. 22b are schematic illustrations of possible embodiments for computers.
Figure 22B:
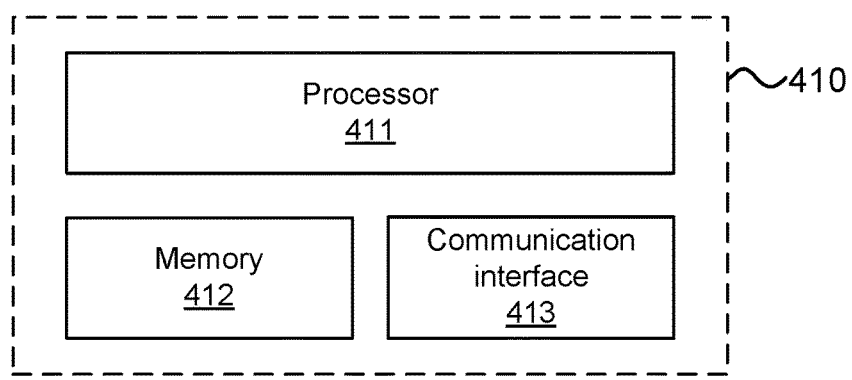

FIG. 22a and FIG. 22b are schematic illustrations of possible embodiments for computers (400, 410) that are able to realize one or more of the embodiments discussed herein that include a "computer". The computer (400, 410) may be implemented in various ways, such as, but not limited to, a server, a client, a personal computer, a network device, a handheld device (e.g., a smartphone), an HMS (such as smart glasses, an augmented reality system, and/or a virtual reality system), a computing device embedded in a wearable device (e.g., a smartwatch or a computer embedded in clothing), a computing device implanted in the human body, and/or any other computer form capable of executing a set of computer instructions. Herein, an augmented reality system refers also to a mixed reality system. Further, references to a computer or processor include any collection of one or more computers and/or processors (which may be at different locations) that individually or jointly execute one or more sets of computer instructions. For example, a first computer may be embedded in the HMS that communicates with a second computer embedded in the user's smartphone that communicates over the Internet with a cloud computer.

The computer 400 includes one or more of the following components: processor 401, memory 402, computer readable medium 403, user interface 404, communication interface 405, and bus 406. The computer 410 includes one or more of the following components: processor 411, memory 412, and communication interface 413.

Functionality of various embodiments may be implemented in hardware, software, firmware, or any combination thereof. If implemented at least in part in software, implementing the functionality may involve a computer program that includes one or more instructions or code stored or transmitted on a computer-readable medium and executed by one or more processors. Computer-readable media may include computer-readable storage media, which corresponds to a tangible medium such as data storage media, or communication media including any medium that facilitates transfer of a computer program from one place to another. Computer-readable medium may be any media that can be accessed by one or more computers to retrieve instructions, code, data, and/or data structures for implementation of the described embodiments. A computer program product may include a computer-readable medium. In one example, the computer-readable medium 403 may include one or more of the following: RAM, ROM, EEPROM, optical storage, magnetic storage, biologic storage, flash memory, or any other medium that can store computer readable data.

A computer program (also known as a program, software, software application, script, program code, or code) can be written in any form of programming language, including compiled or interpreted languages, declarative or procedural languages. The program can be deployed in any form, including as a standalone program or as a module, component, subroutine, object, or another unit suitable for use in a computing environment. A computer program may correspond to a file in a file system, may be stored in a portion of a file that holds other programs or data, and/or may be stored in one or more files that may be dedicated to the program. A computer program may be deployed to be executed on one or more computers that are located at one or more sites that may be interconnected by a communication network.

Computer-readable medium may include a single medium and/or multiple media (e.g., a centralized or distributed database, and/or associated caches and servers) that store one or more sets of instructions. In various embodiments, a computer program, and/or portions of a computer program, may be stored on a non-transitory computer-readable medium, and may be updated and/or downloaded via a communication network, such as the Internet. Optionally, the computer program may be downloaded from a central repository, such as Apple App Store and/or Google Play. Optionally, the computer program may be downloaded from a repository, such as an open source and/or community run repository (e.g., GitHub).

As used herein, references to "one embodiment" (and its variations) mean that the feature being referred to may be included in at least one embodiment of the invention. Moreover, separate references to "one embodiment", "some embodiments", "another embodiment", "still another embodiment", etc., may refer to the same embodiment, may illustrate different aspects of an embodiment, and/or may refer to different embodiments.

Some embodiments may be described using the verb "indicating", the adjective "indicative", and/or using variations thereof. Herein, sentences in the form of "X is indicative of Y" mean that X includes information correlated with Y, up to the case where X equals Y. Stating that "X indicates Y" or "X indicating Y" may be interpreted as "X being indicative of Y". Additionally, sentences in the form of "provide/receive an indication indicating whether X happened" may refer herein to any indication method, including but not limited to: sending/receiving a signal when X happened and not sending/receiving a signal when X did not happen, not sending/receiving a signal when X happened and sending/receiving a signal when X did not happen, and/or sending/receiving a first signal when X happened and sending/receiving a second signal X did not happen.

Herein, "most" of something is defined as above 51% of the something (including 100% of the something). Both a "portion" of something and a "region" of something refer herein to a value between a fraction of the something and 100% of the something. For example, sentences in the form of a "portion of an area" may cover between 0.1% and 100% of the area. As another example, sentences in the form of a "region on the user's forehead" may cover between the smallest area captured by a single pixel (such as 0.1% or 5% of the forehead) and 100% of the forehead. The word "region" refers to an open-ended claim language, and a camera said to capture a specific region on the face may capture just a small part of the specific region, the entire specific region, and/or a portion of the specific region together with additional region(s).

The terms "comprises," "comprising," "includes," "including," "has," "having", or any other variation thereof, indicate an open-ended claim language that does not exclude additional limitations. The "a" or "an" is employed to describe one or more, and the singular also includes the plural unless it is obvious that it is meant otherwise. For example, "a computer" refers to one or more computers, such as a combination of a wearable computer that operates together with a cloud computer.

The phrase "based on" is intended to mean "based, at least in part, on". Additionally, stating that a value is calculated "based on X" and following that, in a certain embodiment, that the value is calculated "also based on Y", means that in the certain embodiment, the value is calculated based on X and Y.

The terms "first", "second" and so forth are to be interpreted merely as ordinal designations, and shall not be limited in themselves. A predetermined value is a fixed value and/or a value determined any time before performing a calculation that compares a certain value with the predetermined value. A value is also considered to be a predetermined value when the logic, used to determine whether a threshold that utilizes the value is reached, is known before start performing computations to determine whether the threshold is reached.

The embodiments of the invention may include any variety of combinations and/or integrations of the features of the embodiments described herein. Although some embodiments may depict serial operations, the embodiments may perform certain operations in parallel and/or in different orders from those depicted. Moreover, the use of repeated reference numerals and/or letters in the text and/or drawings is for the purpose of simplicity and clarity and does not in itself dictate a relationship between the various embodiments and/or configurations discussed. The embodiments are not limited in their applications to the order of steps of the methods, or to details of implementation of the devices, set in the description, drawings, or examples. Moreover, individual blocks illustrated in the figures may be functional in nature and therefore may not necessarily correspond to discrete hardware elements.

Certain features of the embodiments, which may have been, for clarity, described in the context of separate embodiments, may also be provided in various combinations in a single embodiment. Conversely, various features of the embodiments, which may have been, for brevity, described in the context of a single embodiment, may also be provided separately or in any suitable sub-combination. Embodiments described in conjunction with specific examples are presented by way of example, and not limitation. Moreover, it is evident that many alternatives, modifications, and variations will be apparent to those skilled in the art. It is to be understood that other embodiments may be utilized and structural changes may be made without departing from the scope of the embodiments. Accordingly, this disclosure is intended to embrace all such alternatives, modifications, and variations that fall within the spirit and scope of the appended claims and their equivalents.

We claim:

1. A system configured to calculate blood pressure, comprising:
   a first inward-facing head-mounted camera ($HCAM_1$) configured to capture images of a first region of interest ($ROI_1$) located on the face below the eyes and above the lips ($IM_{ROI1}$) of a user;
   a second inward-facing head-mounted camera ($HCAM_2$) configured to capture images of a second region of interest ($ROI_2$) comprising a portion of a temple and/or forehead ($IM_{ROI2}$) of the user; and
   a computer configured to calculate a blood pressure value for the user based on first and second imaging photoplethysmographic signals ($iPPG_1$, $iPPG_2$) recognizable in $IM_{ROI1}$ and $IM_{ROI2}$, respectively.

2. The system of claim 1, wherein $iPPG_1$ and $iPPG_2$ are indicative of pulse arrival times at $ROI_1$ and $ROI_2$, respectively; and wherein the computer is further configured to extract $iPPG_1$ and $iPPG_2$ from $IM_{ROI1}$ and $IM_{ROI2}$, respectively, and to calculate the blood pressure value based on a magnitude of a difference in the pulse arrival times at $ROI_1$ and $ROI_2$.

3. The system of claim 2, wherein the computer is further configured to utilize calibration measurements of the user's blood pressure, taken by a different device, to calculate parameters that are utilized by the computer to calculate the blood pressure value based on $iPPG_1$ and $iPPG_2$; whereby the calibration measurements are indicative of the differences between the pulse arrival times at $ROI_1$ and $ROI_2$ that correspond to different blood pressure values of the user.

4. The system of claim 1, wherein the blood pressure value is indicative of one or more of the following values: the systolic blood pressure of the user, the diastolic blood pressure of the user, and the mean arterial pressure of the user.

5. The system of claim 1, wherein $ROI_2$ comprises a portion of the right temple and/or the right side of the forehead, and further comprising a third inward-facing head-mounted camera ($HCAM_3$) configured to capture images of a third region of interest ($ROI_3$) comprising a portion of the left temple and/or the left side forehead ($IM_{ROI3}$) of the user; and wherein the computer is further configured to extract from $IM_{ROI3}$ a third imaging photoplethysmographic signal ($iPPG_3$) and to calculate the blood pressure value of the user also based on $iPPG_3$ (in addition to $iPPG_1$ and $iPPG_2$).

6. The system of claim 1, wherein $HCAM_1$ is a video camera, and $HCAM_1$ does not occlude the first region of interest.

7. The system of claim 1, wherein $HCAM_1$ is an angle-sensitive pixel sensor camera, weighing less than 1 g.

8. The system of claim 1, wherein the center of $ROI_1$ is located more than 6 cm away from the center of $ROI_2$; whereby changes in $IM_{ROI1}$ that are due to a cardiac pulse wave occur at least 10 ms before, or at least 10 ms after, changes in $IM_{ROI2}$ occur, which are due to the same cardiac pulse wave.

9. The system of claim 1, wherein the computer is further configured to generate feature values based on data comprising $IM_{ROI1}$ and $IM_{ROI2}$, and to utilize a model to calculate the blood pressure value based on the feature values; wherein the model was generated based on training data comprising: previously taken $IM_{ROI1}$ and $IM_{ROI2}$, and blood pressure values measured at times corresponding to the previously taken $IM_{ROI1}$ and $IM_{ROI2}$.

10. The system of claim 9, wherein $iPPG_1$ and $iPPG_2$ are indicative of pulse arrival times at $ROI_1$ and $ROI_2$, respectively; wherein the computer is further configured to extract $iPPG_1$ and $iPPG_2$ from $IM_{ROI1}$ and $IM_{ROI2}$, respectively; and wherein the feature values comprise a value that is indicative of a difference between when a pulse wave manifested in $IM_{ROI1}$ and $IM_{ROI2}$.

11. The system of claim 9, wherein $iPPG_1$ and $iPPG_2$ are indicative of pulse arrival times at $ROI_1$ and $ROI_2$, respectively; wherein the computer is further configured to extract $iPPG_1$ and $iPPG_2$ from $IM_{ROI1}$ and $IM_{ROI2}$, respectively; and wherein the feature values comprise one or more values that are indicative of: (i) a certain blood pressure value of the user that was measured during a certain previous period, and (ii) a difference between when pulse waves of the user manifested in $IM_{ROI1}$ and $IM_{ROI2}$ taken during the certain previous period.

12. The system of claim 9, wherein the previously taken $IM_{ROI1}$ and $IM_{ROI2}$ comprise images of body parts of the user, and the blood pressure values corresponding to the previously taken $IM_{ROI1}$ and $IM_{ROI2}$ are blood pressure values of the user measured using a device that does not utilize $HCAM_1$ and $HCAM_2$.

13. The system of claim 9, wherein the computer is further configured to: receive a value indicative of a stress level of the user, and generate at least one of the feature values based on the received value.

14. The system of claim 13, further comprising an inward-facing head-mounted thermal camera configured to take thermal measurements of at least one of the following regions on the user's face: a periorbital region, a region on the forehead, and a region on the nose; whereby the thermal measurements are indicative of the stress level of the user.

15. The system of claim 9, wherein the computer is further configured to: receive a value indicative of a hydration level of the user, and generate at least one of the feature values based on the received value.

16. The system of claim 15, further comprising an additional camera configured to detect intensity of radiation that is reflected from a region of exposed skin of the user; wherein the radiation is in spectral wavelengths chosen to be preferentially absorbed by tissue water, and are chosen from three primary bands of wavelengths of approximately 1100-1350 nm, approximately 1500-1800 nm, and approximately 2000-2300 nm.

17. The system of claim 9, wherein the computer is further configured to: receive a value indicative of a temperature of the user's body, and generate at least one of the feature values based on the received value.

18. The system of claim 9, wherein the computer is further configured to: receive a value indicative of the movement of the user's body, and generate at least one of the feature values based on the received value.

19. The system of claim 9, wherein the computer is further configured to: receive a value indicative of an orientation of the user's head, and generate at least one of the feature values based on the received value.

20. The system of claim 9, wherein the computer is further configured to: receive a value indicative of consumption of a substance by the user, and generate at least one of the feature values based on the received value; and wherein the substance comprises one or more of the following: a vasodilator, a vasoconstrictor.

* * * * *